United States Patent
Wu et al.

(10) Patent No.: US 11,345,697 B1
(45) Date of Patent: May 31, 2022

(54) CRYSTALLINE BERBERINE ASCORBATE SALT, METHODS OF PREPARATION AND APPLICATIONS THEREOF

(71) Applicants: Dedong Wu, Waban, MA (US); Alex Wu, Waban, MA (US)

(72) Inventors: Dedong Wu, Waban, MA (US); Alex Wu, Waban, MA (US)

(73) Assignee: Beiture LLC, Waban, MA (US)

( * ) Notice: Subject to any disclaimer, the term of this patent is extended or adjusted under 35 U.S.C. 154(b) by 0 days.

(21) Appl. No.: 17/118,134

(22) Filed: Dec. 10, 2020

(51) Int. Cl.
*C07D 455/03* (2006.01)
*C07D 307/62* (2006.01)

(52) U.S. Cl.
CPC ......... *C07D 455/03* (2013.01); *C07D 307/62* (2013.01); *C07B 2200/13* (2013.01)

(58) Field of Classification Search
None
See application file for complete search history.

(56) References Cited

U.S. PATENT DOCUMENTS 10,577,379 B1    3/2020    Xie et al.

FOREIGN PATENT DOCUMENTS

CN    111205285    5/2020

OTHER PUBLICATIONS

Grant& Hackh's Chemical Dictionary (5th Ed. 1987) at p. 148.*
CAPLUS printout of "Davidyants et al., Preparation of berberine salts of physiologically active acids. Doklady Akademii Nauk Tadzhikskoi SSR, 1963, 6, p. 36-38."*
Chemical Abstract Registry No. 299-36-5, indexed in the Registry File on STN CAS Online Nov. 16, 1984.*
Dostal, J. et al., "Berberine and coptisine free bases", Journal of Molecular Structure, 2004, 687, 135-142.

* cited by examiner

*Primary Examiner* — Po-Chih Chen

(57) ABSTRACT

The present disclosure relates to crystalline berberine ascorbate salts and crystalline ketone berberine adducts, which can be used in preparing pharmaceutical or dietary compositions for the treatment or prevention of bacterial infections, cardiovascular diseases or other conditions. The present disclosure also relates to methods of preparing crystalline berberine ascorbate or other berberine salts by reaction crystallization using one or more of crystalline berberine ketone adducts as a starting material.

11 Claims, 14 Drawing Sheets

CRYSTALLINE BERBERINE ASCORBATE SALT, METHODS OF PREPARATION AND APPLICATIONS THEREOF

FIELD OF THE INVENTION

The present disclosure relates to crystalline berberine ascorbate salts and crystalline ketone berberine adducts, which can be used in a pharmaceutical or dietary composition for the treatment or prevention of bacterial infections, cardiovascular diseases or other conditions. The present disclosure also relates to methods of preparing crystalline berberine ascorbate or other salts by reaction crystallization using one or more of crystalline berberine ketone adducts disclosed herein as starting material.

BACKGROUND OF THE INVENTION

Berberine, named as 5,6-dihydro-9,10-dimethoxybenzo[g]-1,3-benzodioxolo[5,6-a]quinolizinium, is a quaternary benzylisoquinoline alkaloid, which is found in the roots, rhizomes, stems and bark of many medicinally important plants. Berberine is clinically used as an antibacterial agent toward gastrointestinal infections for treatment of diarrhea. Recent clinical investigations on berberine have also demonstrated a wide spectrum of pharmacological effects, including antihypertensive, antiarrhythmic, antihyperglycemic, anticancer, antidepressant, anxiolytic, neuroprotective, antioxidant, anti-inflammatory, analgesic, and hypolipidemic activities.

The drug substance form of berberine in commercial pharmaceutical products or dietary supplements commonly uses berberine chloride dihydrate. Berberine chloride as a dihydrate form could lose more than 8% of the water in an elevated temperature or a low humidity environment. On the other hand, it also could uptake about 8% of water and convert to a tetrahydrate form of berberine chloride in water or a high humidity environment. Thus, there are various challenges to control the water content in berberine chloride during manufactures of the drug substance and/or the drug product. In addition, crystalline berberine chloride is poorly soluble in water, which results a low in vivo exposure and potentially limits its therapeutic activities. Furthermore, its nearly 10% chloride anion component in berberine chloride is a potential hazard for patients with Type 2 diabetes.

Therefore, it is desirable to identify an alternative solid salt form of berberine that has better physicochemical property for manufacture processes of the drug substance and the drug product. It is also important to obtain an alternative solid salt form of berberine that possesses improved pharmaceutical properties, e.g. solubility, for potential clinical use to enhance its therapeutic activity.

Berberine exists as a cation and is usually commercially available as a salt, e.g. hydrochloride salt or berberine sulfate salt. These berberine salt cannot be directly used in a traditional salt screen to identify various berberine salt for solid-state property and biopharmaceutical property assessments. Nevertheless, it is extremely difficult if not impossible to prepare a neutralized molecule of berberine, e.g. berberine hydroxide form, as starting material for a salt screening or a salt preparation. This is because the assumed berberine hydroxide form is chemically unstable, and various degraded compounds, 8-hydroxy-7,8-dihydroberberine, 8-oxoberberine, bis(7,8-dihydroberberin-8-yl) ether, were observed and characterized by single crystal structure analysis when berberine chloride or berberine sulphate was titrated with sodium hydroxide. (Reference: Journal of Molecular Structure, 2004, 687, 135-142).

Accordingly, it is an objective of the disclosure to identify a method to prepare various berberine salts, allowing a salt screen to identify a suitable berberine salt that has an improved chemical purity, or crystallinity, or solid state property, or solubility, or dissolution rate.

It is also an objective of this disclosure to provide a method and appropriate starting materials to prepare, scale up and manufacture the desire berberine salt for pharmaceutical development.

It is well known that crystalline forms of a drug candidate have significant impact on physicochemical property of a drug substance, for example, crystallinity, thermal stability and hygroscopicity. An optimized crystalline form of an alternative berberine salt is necessary for an acceptable chemical purity profile for quality control and a suitable physical property for manufacture of the drug substance and drug product.

Thus, it is an additional objective of this disclosure to provide pharmaceutical compositions comprising the optimal crystalline form of berberine salts disclosed herein.

Other objects, advantages and features of the present disclosure will become apparent from the following specification taken in conjunction with the accompanying examples or drawings.

BRIEF SUMMARY OF THE INVENTION

Provided herein is a crystalline berberine ascorbate salt. Crystalline berberine ascorbate comprises berberine as a cation and neutralized ascorbic acid as an anion, wherein the berberine and the neutralized ascorbate acid have the following chemical structures, respectively:

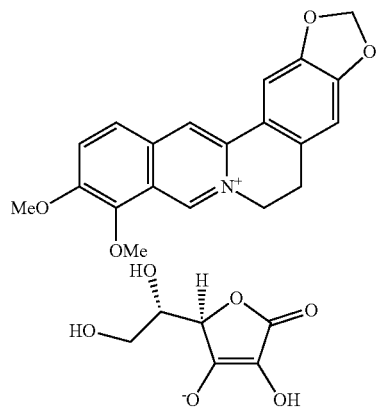

In one aspect, provided herein is a crystalline berberine ascorbate salt. Various crystalline forms of the berberine ascorbate salt are discovered and disclosed herein to demonstrate better physical property and biopharmaceutical property compared to the commercial berberine chloride salt.

In one embodiment as disclosed herein, one of the exemplary crystalline berberine ascorbate salts is an anhydrous form, designated as Form A, and is characterized by an XRPD pattern comprising one or more peaks expressed as 2θ±0.2° of about 6.7°, about 8.6°, about 13.3°, about 15.5°, about 16.4°, about 17.8°, about 18.9°, about 19.7°, about 25.1°, and about 26.2°.

Remarkably, crystalline berberine ascorbate salt Form A disclosed herein demonstrates an optimal physical property as a stable anhydrous form, which benefits manufacture and storage of the drug substance and the drug product.

Surprisingly, crystalline berberine ascorbate Form A shows a much higher aqueous solubility than the commercial berberine hydrochloride, indicating a possible higher in vivo concentration and a better therapeutic activity.

Furthermore, crystalline berberine ascorbate salts disclosed herein eliminates undesired counter ion, specifically, the chloride anion of berberine chloride usually used in a commercially available berberine drug product, so that reducing some side effects caused by the chloride anion.

In another aspect, provided herein is a method to perform a salt screen of various berberine salts and to prepare the desire crystalline berberine ascorbate salt. The disclosed method uses specifically a reaction crystallization process to prepare various crystalline ascorbate salt forms and one or more of berberine ketone adducts as starting material.

The general reaction disclosed herein to prepare the berberine ascorbate salt by a reaction crystallization process is shown as the following scheme:

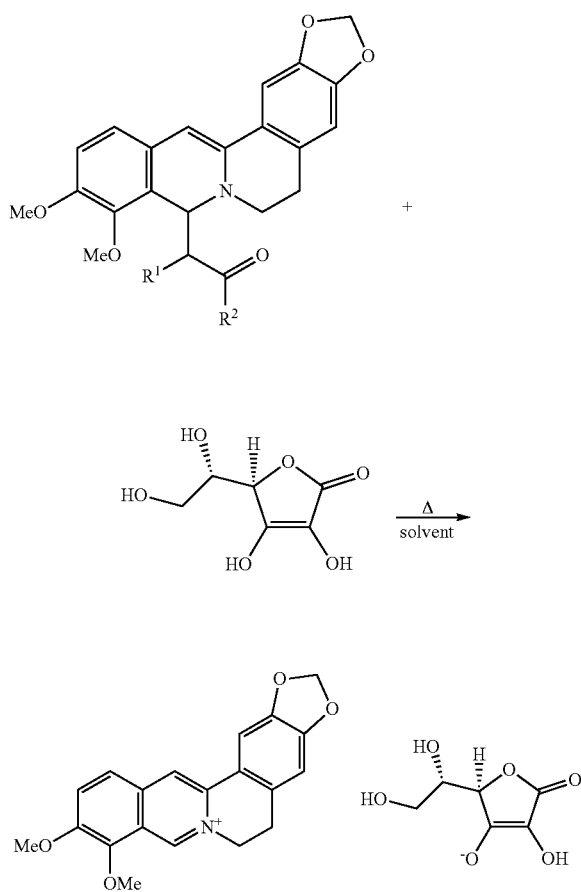

wherein $R^1$ is H, or a $C_1$-$C_5$ alkyl group and $R^2$ is an $C_1$-$C_{10}$ alkyl group or the aryl group or substituted group thereof; or $R^1R^2$ is methylene bridge group, $C_2$-$C_6$ alkylene group, substituted or unsubstituted group thereof.

Exemplary crystalline berberine ketone adducts disclosed herein for reaction crystallization include one or more of berberine ketone adducts wherein $R^1$ is H and $R^2$ is methyl, ethyl, phenyl, isopropyl, isobutyl, or $R^1R^2$=—$(CH_2)_4$—.

The preparation method disclosed herein is a method of reaction crystallization to prepare crystalline berberine ascorbate solid forms, the method comprises suspending one of berberine adducts of ketones, including acetone, methyl ethyl ketone (MEK), methyl phenyl ketone (MPHK), methyl isopropyl ketone (MIPK), methyl isobutyl ketone (MIBK) and cyclohexanone, in an organic solvent (including, but is not limited to, ethanol, isopropanol, acetonitrile, ethyl acetate, tetrahydrofuran, dichloromethane, tertbutyl methyl ether) to obtain a suspension; stirring the suspension in a temperature of about 50-80° C. for about 0.5 to 4 hours; cooling the suspension to room temperature; filtering, washing, and drying to obtain crystalline berberine ascorbate solid form.

In another aspect, various starting materials of berberine ketone adducts were prepared and assessed. A modified reaction condition is used to prepare crystalline forms of previously known compounds, including berberine acetone adduct, berberine methyl ethyl ketone adduct and berberine methyl phenyl ketone adduct. This modified method also allows to prepare some new compounds, including berberine methyl isopropyl ketone adduct, berberine methyl isobutyl ketone adduct and berberine cyclohexanone adduct. Crystalline forms of these new compounds were obtained directly from reaction mixtures at the room temperature.

In one embodiment as disclosed herein, one of the exemplary new berberine ketone compounds is berberine methyl isopropyl ketone adduct. Crystalline berberine methyl isopropyl ketone adduct is prepared through reaction of berberine chloride and ketone in a modified reaction conditions including using a mixture of solvents at the ambient temperature. The crystalline form of berberine methyl isopropyl ketone adduct disclosed herein with the following structure is an anhydrous form and is characterized by an XRPD pattern comprising one or more peaks expressed as 2θ±0.2° of about 9.9°, about 14.7°, about 16.7°, about 17.2°, about 19.8°, about 20.1°, about 21.4°, about 21.8°, about 25.0°, and about 25.3°.

The chemical composition and crystalline form are characterized and confirmed by single crystal X-ray diffraction method. Surprisingly, one of the exemplary new berberine ketone compounds, berberine methyl isopropyl ketone adduct, has a unusually lower melting point of about 85° C., compared to the known berberine acetone adduct with a melting point of about 168° C. Remarkably, by using this new exemplary berberine ketone compound, it is easier to monitor the reaction endpoint by virtually observation of forming a clear solution prior to precipitating berberine ascorbate, compared to using the known crystalline berberine acetone adduct as starting material, in which solid-to-solid conversion from berberine acetone adduct to berberine ascorbate was observed.

In another aspect, the disclosed herein is a method to use crystalline berberine ketone adducts to obtain berberine salts, e.g. berberine chloride, for a better chemical purity profile. This purification method is important when the raw material of berberine chloride has a low chemical purity, e.g. <85% of weight content of berberine chloride in the total weight, and chemical purity profile of the resulting berberine ketone adduct is not good enough as starting material to prepare crystalline berberine ascorbate with acceptable crystallinity and chemical purity. This purification method can be also used convert the berberine chloride crudes to purified berberine chloride with an acceptable chemical purity profile for pharmaceutical or dietary compositions. The general reaction disclosed herein to prepare the berberine chloride salt is shown as the following scheme:

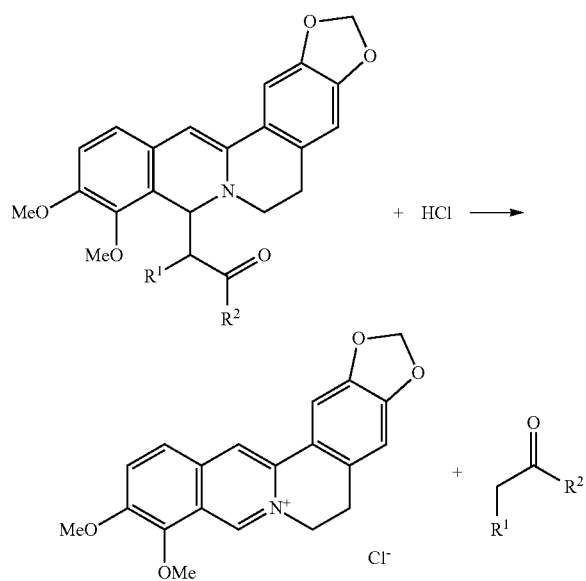

Exemplary crystalline berberine ketone adducts disclosed herein include one or more of berberine ketone adducts wherein $R^1$ is H and $R^2$ is ethyl, phenyl, isopropyl, isobutyl, or $R^1R^2$=—$(CH_2)_4$—.

The general method comprises suspending one of pure crystalline berberine adducts of ketones, including methyl ethyl ketone (MEK), methyl phenyl ketone, methyl isopropyl ketone (MIPK), methyl isobutyl ketone (MIBK) and cyclohexanone in hydrochloric acid aqueous solution; stirring the suspension in a temperature of about 60-100° C. to obtain a brown solution; cooling the solution to room temperature; precipitate the crystalline solid from the solution; filtering, washing, and drying the resulted solid to obtain the pure berberine chloride as a tetrahydrate form.

Surprisingly, by using one of new exemplary berberine ketone compounds, e.g. berberine methyl isopropyl ketone adduct, the product yield of the purified berberine chloride increased to >80% from <50% by using the known crystalline berberine acetone adduct with the same reaction condition.

Remarkably, by using berberine methyl isopropyl ketone adduct, it is easier to monitor the reaction endpoint by virtually observation of forming a clear solution prior to precipitating berberine chloride, compared to using the known crystalline berberine acetone adduct as starting material, in which solid-to-solid conversion from berberine acetone adduct to berberine chloride was observed.

The purified berberine chloride was used as new starting material to prepare crystalline berberine ketone adducts with acceptable chemical purity profile for preparing crystalline berberine ascorbate. This process could be also used in preparation of purified berberine chloride salt or other salts by converting berberine crude into one of berberine ketone adducts, followed by converting to the desired berberine chloride salt or other salts, to achieve a higher chemical purify to be used in pharmaceutical or dietary products.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION OF THE INVENTION

Figure 1:
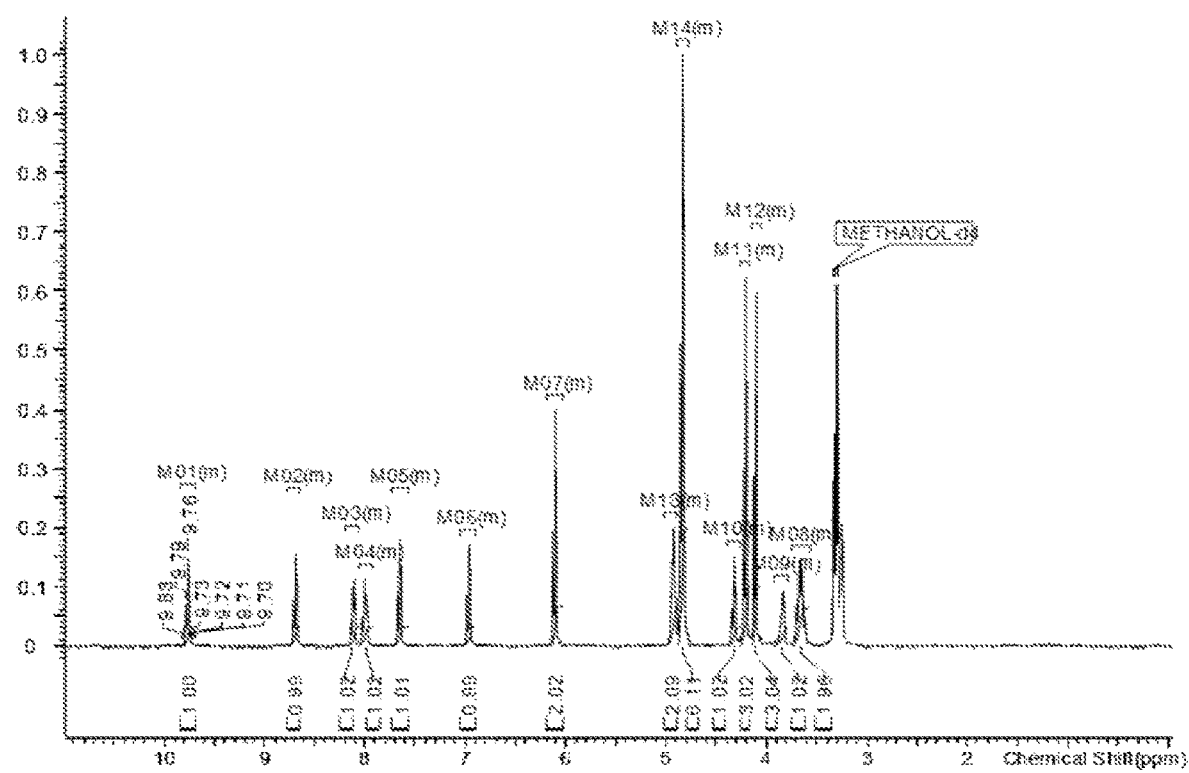
FIG. 1 shows the $^1$H NMR spectrum of crystalline berberine ascorbate Form A.

Commercial pharmaceutical or dietary supplement products are commonly using crystalline berberine chloride dihydrate. The dihydrate form of berberine chloride used in the commercial products has sub-optimal physical and biopharmaceutical properties, e.g. poor thermostability, high hygroscopicity and poor aqueous solubility. It is crucial to identify an alternative salt for berberine with a better chemical purity profile, better physical property and better biopharmaceutical property. It is also necessary to identify a safer alternative counter ion to replace the chloride anion for patients with type 2 diabetes.

The present disclosure relates to crystalline berberine ascorbate salts, which can be used in a pharmaceutical or dietary composition for the treatment or prevention of bacterial infections, cardiovascular diseases or other conditions. Crystalline berberine ascorbate disclosed herein demonstrates a high quality of chemical purity profile suitable to be used in pharmaceutical or dietary supplementary products, an improved physical property which is preferred for manufacture and storage of the drug substance and the drug product, an enhanced aqueous solubility for a potential enhanced drug exposure comparing to the commercial berberine chloride. It also replaced the undesired chloride counter ion with a safer L-ascorbic acid component known as Vitamin C. Various crystalline forms of berberine ascorbate are disclosed herein.

Berberine exists as a cation and is usually commercially available as a salt, e.g. hydrochloride salt or berberine sulfate salt, it is important to identify a method to prepare various berberine salts. Various methods were explored to prepare berberine salts from commercially available berberine salt, including using berberine chloride reaction with sodium ascorbate, however, starting material of berberine chloride precipitated out from reaction mixture because of lower solubility of berberine chloride in water compared to berberine ascorbate. A literature method was reported to prepare berberine ascorbate through extracting the presumed berberine hydroxide followed by reaction with ascorbic acid. (Reference: Doklady Akademii Nauk Tadzhikskoi SSR, 1963, 6(6), 36-38). Only amorphous berberine ascorbate with a high level of degraded impurities was produced. In fact, up to now, there is no report to prepare crystalline berberine ascorbate. This is due to the fact that the assumed berberine hydroxide form is chemically unstable and degraded to various compounds, including 8-hydroxy-7,8-dihydroberberine, 8-oxoberberine, bis(7,8-dihydroberberin-8-yl) ether (Reference: Journal of Molecular Structure, 2004, 687, 135-142). These impurities in amorphous berberine ascorbate crude prohibited crystal nucleation and/or crystal growth, thus a recrystallization process did not yield a crystalline berberine ascorbate with better purity profile.

The present disclosure also relates methods of preparing crystalline berberine salts or berberine ascorbate solid forms via reaction crystallization using one of berberine ketone adducts as a starting material. The disclosed methods were used to identify a suitable berberine salt that has an improved chemical purity, or crystallinity, or solid-state property, or solubility, or dissolution rate. About 40 berberine salts comprising various acidic counter ions were screened by using the reaction crystallization process and berberine ketone adduct. After about 8 crystalline salt hits were prepared for solid state property and solubility assessments, crystalline berberine ascorbates were chosen for further assessments.

The present disclosure also relates to crystalline berberine ketone adducts, which are used as starting materials to prepare, scale up and manufacture the desire berberine ascorbate salt or other salts for pharmaceutical development. Exemplary crystalline berberine ketone adducts disclosed herein include crystalline forms of previously known compounds, including berberine acetone adduct, berberine methyl ethyl ketone adduct and berberine methyl phenyl ketone adduct. Exemplary crystalline berberine ketone adducts disclosed herein also include some new compounds, including berberine methyl isopropyl ketone adduct, berberine methyl isobutyl ketone adduct and berberine cyclohexanone adduct. The preparation methods disclosed herein represent a robust process for preparing crystalline berberine ascorbate or other berberine salts, starting with appreciate berberine ketone adduct.

Furthermore, crystalline berberine ketone adducts prepared from versatile ketones offer a broad range of selections to optimize product purity and process yield in manufacture of the crystalline berberine ascorbate salt and other berberine salts. Methods to purify berberine ketone adducts were identified by converting the berberine ketone adducts back to berberine chloride but with better chemical purity.

The embodiments of this disclosure are not limited to any compositions and methods, which can vary and are understood by skilled artisans. So that the present disclosure may be more readily understood, certain terms are first defined. Unless defined otherwise, all technical and scientific terms used herein have the same meaning as commonly understood by one of ordinary skill in the art to which embodiments of the disclosure pertain. Many methods and materials similar, modified, or equivalent to those described herein can be used in the practice of the embodiments of the present disclosure without undue experimentation, the preferred materials and methods are described herein. In describing and claiming the embodiments of the present disclosure, the following terminology will be used in accordance with the definitions set out below.

Crystalline Berberine Ascorbate Salt

The crystalline salt disclosed herein is a crystalline berberine ascorbate salt. Berberine is a molecule (cation) with the following structure.

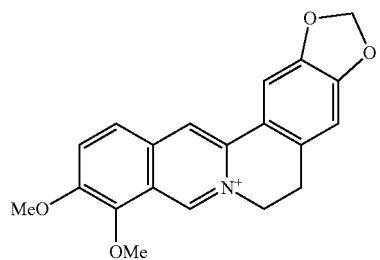 [SMILES: COc1ccc2cc3[n+](cc2c1OC)CCc1cc2c(cc1-3)OCO2]

Ascorbic acid, or L-ascorbic acid, also known as vitamin C, is a molecule with the following structure.

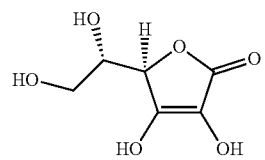

A neutralized ascorbic acid, or ascorbate as referred herein, is an anion having the following structure.

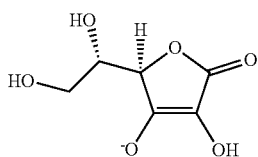

Berberine is found in the roots, rhizomes, stems and bark of many medicinally important plants and clinically used as an antibacterial agent toward gastrointestinal infections for treatment of diarrhea. Berberine has also been used as a herbal medicine and a dietary supplement for various health benefits. Notably, berberine is regarded as a potential novel cholesterol-lowering medicine working through a unique mechanism distinct from statins, the most used cholesterol-lowering drugs. It is also found to be effective for diabetes mellitus treatment, representing a promising drug candidate as an alternative of metformin, the first-line medication for the treatment of type 2 diabetes.

L-ascorbic acid and ascorbate in its salt form, also known as vitamin C, is a vitamin found in various foods and sold as a dietary supplement. Vitamin C is an essential nutrient used to prevent and treat various diseases. Vitamin C is generally well tolerated and may be taken by mouth or by injection with the ascorbic acid or its ascorbate salt form. The GRAS status (Generally Recognized As Safe) of Vitamin C allows to use it as a salt former to improve physical and biopharmaceutical property for potential drug candidates, e.g. berberine cation.

A berberine ascorbate salt, as used herein, is referred to a crystalline salt having a formula of

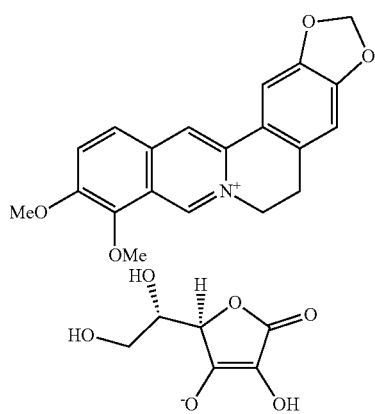

In one aspect, provided herein is a crystalline berberine ascorbate salt. Crystalline berberine ascorbate as disclosed herein comprising the berberine as a cation and the neutralized ascorbic acid (ascorbate) as an anion, wherein the salt has a molar ratio of the berberine and the ascorbate of about 0.9:1 to about 1:0.9; wherein the salt is a crystalline solid of at least 75% crystalline material.

A crystalline solid can be a material containing a single component or multiple components. Crystalline solid includes, but is not limited to, a polymorph, a solvate (including hydrate), a salt, a cocrystal, a single crystalline form, or a mixture thereof. In some embodiments, a crystalline solid is crystalline as determined, e.g., by XRPD, solid NMR, Raman spectroscopy, polarized light microscopy (PLM), thermal analysis, and/or moisture absorption analysis. In some embodiments, a crystalline solid comprises about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, about 100%, or any value there between of crystalline material. In some embodiments, a crystalline solid of a substance may be substantially free of or free of an amorphous form. In some embodiments, a crystalline solid of a substance may be "physically pure," e.g., contains less than about 5%, about 10%, about 15%, about 20%, about 25%, about 30%, about 35%, or about 40% of other crystal forms or amorphous forms on a weight basis. In some embodiments, a crystal form of a substance may be "chemically pure," e.g. contains less than about 1%, about 2%, about 3%, about 4%, about 5%, about 6%, about 7%, about 8%, about 9%, about 10%, about 15%, about 20%, about 25%, about 30%, about 35%, or about 40% of other chemical substances on a weight basis.

A "salt", as used herein, refers to a solid comprising both anions and cations in equal molar amount. A salt can be a "single-component" solid. A salt can also be a "multiple-component" solid comprising one or more additional species, such as nonionic molecules, cocrystal molecules, and/or solvent molecules. For example, a crystalline multiple-component salt further comprises one or more non-covalently bonded species at regular positions in its crystal lattice.

The term "solid form", "solid", or related terms, as used herein, refers to a physical form that is not predominantly in a liquid or a gaseous state. A solid form may be crystalline, amorphous, or a mixture thereof.

The term "amorphous," "amorphous form," or related terms refers to a substance, component, or product that is not crystalline as determined by X-ray diffraction, solid NMR, or other analytical techniques as known by one skilled in the art. In particular, the term "amorphous form" describes a disordered solid form, e.g. a solid form lacking long range crystalline order.

The term "crystalline", "crystalline solid", "crystal solid", "crystal form", "crystalline form", or related terms, as used herein, refers to any solid substance, material, compound, a mixture of compounds, or product exhibiting three-dimensional order, which is in contrast to an amorphous solid substance, giving a distinctive PXRD pattern or solid NMR spectrum with sharply defined peaks.

The terms "polymorphs," "polymorphic forms", or related terms refer to a crystalline solid comprising two or more crystal forms of the same molecule, mixtures of molecules, salt, or combination thereof.

The term "anhydrous form" or "neat form" refers to a solid form of a substance which contains only acidic counter ion and the basic counter ion of the salt.

The term "solvate" refers to the existence of more than one crystal forms for a particular solvate composition. Similarly, "hydrate" or "hydrate form" refers to the existence of more than one crystal forms for a particular hydrate composition. The term "desolvated solvate" refers to a crystal form of a substance which may be prepared by removing the solvent from a solvate.

A berberine ascorbate salt was obtained and chosen from a salt screen of using various acidic counter ions, followed by scale up of crystalline hits for solid-state property and solubility assessment. Various crystalline forms, including anhydrous form (or neat from), solvate, hydrate of berberine ascorbate were identified and disclosed herein. An optimal solid form of crystalline berberine ascorbate was selected based on its physicochemical property and biopharmaceutical property.

Remarkably, a stable anhydrous form of crystalline berberine ascorbate designated as Form A was obtained from reaction crystallization as disclosed herein. Crystalline berberine ascorbate Form A demonstrated an optimal physical property, e.g. thermal stability. There was no significant weight loss for Form A in thermal study even when it was heated to about 150° C. Form A started to melt and/or decompose only at above 175° C. Anhydrous Form A also demonstrated a non-hygroscopic property up to 70% relative humidity without a form change. The thermal stability and non-hygroscopicity of crystalline berberine ascorbate Form A would benefit manufacture, quality control and storage of the drug substance and the drug product.

Surprisingly, crystalline berberine ascorbate Form A disclosed herein showed more than 50 times higher aqueous solubility than that of the commercial berberine hydrochloride. 50 mg of crystalline berberine ascorbate Form A was rapidly dissolved in 0.20 ml of water to get a clear yellow solution within about 10 minutes, while 50 mg of berberine chloride was suspended in 10 ml of water and retained as a yellow suspension after stirring at the room temperature for about 1 day. The better aqueous solubility of crystalline berberine ascorbate Form A indicates a possible higher in vivo concentration, which could result in better therapeutic activities.

As disclosed herein, crystalline berberine ascorbate Form A obtained directly from the reaction crystallization process provided berberine salt with a high crystallinity and a high chemical purity profile. Other crystalline forms of berberine ascorbate, e.g., Form B, Form C, or Form D, were obtained with a lower crystallinity and a poor chemical purity profile.

X-ray powder diffraction (XRPD) technique is regarded as the "golden tool" for identifying, analyzing, and/or characterizing crystalline forms. It also provides a fingerprint for each crystalline form with unique molecular conformation and molecular packing in its crystal lattice. The crystalline salts disclosed herein were characterized by X-ray powder diffraction technique and found to have unique XRPD patterns, respectively.

The term "powder X-ray diffraction pattern", "X-ray powder diffraction pattern", "PXRD pattern", "XRPD pattern", or "powder X-ray diffraction diagram" refers to the experimentally observed diffractogram or parameters derived therefrom. Powder X-ray diffraction patterns are characterized by peak positions (abscissa) and peak intensities (ordinate). The term "2 theta value" or "2θ" refers to the peak position in degrees based on the experimental setup of the X-ray diffraction experiment and is a common abscissa unit in diffraction patterns. The experimental setup requires that if a reflection is diffracted when the incoming beam forms an angle theta (θ) with a certain lattice plane, the reflected beam is recorded at an angle 2 theta (2θ). The reference herein to specific 2θ values for a specific solid form is intended to mean the 2θ values (in degrees) as measured using the X-ray diffraction experimental conditions as described herein.

In one embodiment as disclosed herein, crystalline berberine ascorbate is an anhydrous form, designated as Form A, and is characterized by an XRPD pattern comprising one or more peaks expressed as 2θ±0.2° of about 6.7°, about 8.6°, about 13.3°, about 15.5°, about 16.4°, about 17.8°, about 18.9°, about 19.7°, about 25.1°, and about 26.2°.

In another embodiment, crystalline berberine ascorbate disclosed herein is a hydrate form, designated as Form B, and is characterized by an XRPD pattern comprising one or more peaks expressed as 2θ±0.2° of about 6.9°, about 14.8°, about 15.8°, about 19.1°, about 20.2°, about 20.7°, about 25.2°, about 25.7°, about 26.4°, and about 27.7°.

In another embodiment, the crystalline berberine ascorbate salt disclosed herein is a crystalline Form C, and is characterized by an XRPD pattern comprising one or more peaks expressed as 2θ±0.2° of about 6.8°, about 8.4°, about 10.8°, about 14.0°, about 14.7°, about 15.0°, about 15.8°, about 16.9°, about 25.2°, and about 25.5°.

In another embodiment, the crystalline berberine ascorbate salt disclosed herein is a crystalline Form D, and is characterized by an XRPD pattern comprising one or more peaks expressed as 2θ±0.2° of about 6.9°, about 12.7°, about 14.1°, about 14.5°, about 16.1°, about 16.5°, about 19.0°, about 20.7°, about 25.6°, and about 26.7°.

Method of Preparing Crystalline Berberine Ascorbate

It is important to develop a robust process method to prepare berberine salts. Some berberine salts, for example, berberine organic salts, were prepared through anion exchanges starting with berberine chloride. After being dissolved in the hot water, berberine chloride reacted with alternative acids in their neutralized forms, usually their sodium or potassium salts, and then cooled down to precipitate the desire alternative salts. (Reference examples: Cryst. Growth Des. 2016, 16, 933-939; U.S. Pat. No. 10,577, 379 B1 Mar. 2020 Xie et al.) This method took advantage by directly precipitating the desired berberine salt without extracting unstable berberine hydroxide as an intermediate. However, such a method only produced alternative berberine salts with lower aqueous solubility compared to starting material of berberine salts, e.g. berberine chloride. Due to the poor aqueous solubility of berberine chloride in the cold water, this method only limited to preparation of an alternative organic salt of berberine whose aqueous solubility is low enough to allow it to precipitate out from reaction mixtures. By applying such a method to prepare berberine ascorbate, only berberine chloride precipitated out from the reaction mixture. Thus, this commonly used method was not suitable to prepare berberine ascorbate because berberine ascorbate has a much higher aqueous solubility compared to that of berberine chloride.

The only literature method to prepare a berberine ascorbate salt was found by converting berberine chloride to its hydroxide form by using sodium hydroxide (NaOH) aqueous solution and then extracted with ether solvent, followed by reacting with ascorbic acid. The presumed berberine hydroxide form, which has not been isolated as a pure form, was known to exist as berberine keto-enol tautomerism in a basic condition. The chemical equilibrium between a keto form (an aldehyde) and an enol (an alcohol) makes the assumed berberine hydroxide prone to decompose to generate significant amounts of various impurities. In fact, the "free base" of quaternary berberine was later found to be unstable 8-hydroxy protoberberine as the major components with other degraded impurities, e.g. 8-oxoberberine and bis(7,8-dihydroberberin-8-yl) ether (Reference: Journal of Molecular Structure, 2004, 687, 135-142). These impurities not only made it difficult to prepare a pure berberine ascorbate salt but also inhibited crystallization process to obtain a crystalline form of berberine ascorbate from the reaction mixture and/or during recrystallization. Amorphous gel-like solid or predominately amorphous material was usually obtained from the reaction mixture of the assumed berberine hydroxide with the ascorbic acid. Recrystallization of the crude berberine ascorbate only produced amorphous solid or hemi-crystalline solid with an even higher level of impurities, because the berberine ascorbate was unstable when being dissolved in a solution, especially being heated to an elevated temperature for an extended period. New chemical impurities were also generated and identified during recrystallization process of berberine ascorbate.

In order to stabilize the neutralized berberine form, the berberine acetone adduct comprising an acetyl group attached to the dihydroberberine molecule, was selected as starting material to screen and prepare berberine ascorbate salt. Berberine acetone adduct was prepared and used as the intermediates to prepare other substituted berberine derivatives. The berberine acetone adduct was also used in preparation alternative organic salts of berberine from acids with strong acidity, including benzenesulfonic acid, di-carboxylic acids and tri-carboxylic acid (Journal of Asian Natural Products Research, 2016, 18(6), 576-586) and purifying berberine chloride (CN 111205285 pending/2020 Xie et al.).

As disclosed herein, for the first time, crystalline berberine acetone adduct is used in reaction crystallization process for preparing crystalline berberine ascorbate by reacting with L-ascorbic acid, a special natural organic compound that lacks carboxylic functional group. Surprisingly, crystalline berberine ascorbate is produced despite of that the ascorbic acid is lack of carboxylic functional group and has a much lower acidity (higher pKa value) compared to other acids used previously.

In another aspect, disclosed herein is a method to prepare crystalline berberine ascorbate by using reaction crystallization process and one of berberine ketone adducts as starting material. The reaction crystallization uses one of berberine ketone adducts as starting material to react with ascorbic acid and then directly precipitates crystalline berberine ascorbate from the reaction mixture. An exemplary reaction crystallization scheme to prepare crystalline berberine ascorbate is shown below.

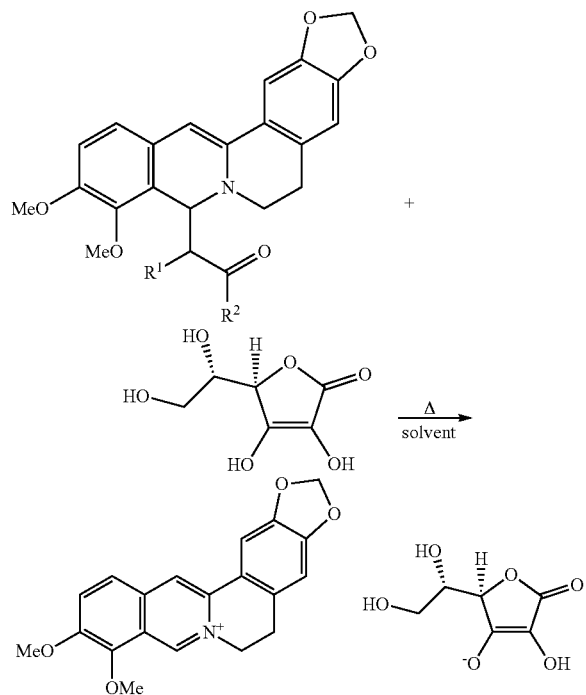

wherein $R^1$ is H, or a $C_1$-$C_5$ alkyl group and $R^2$ is an $C_1$-$C_{10}$ alkyl group or the aryl group or substituted group thereof; or $R^1R^2$ is methylene bridge group, $C_2$-$C_6$ alkylene group, substituted or unsubstituted group thereof.

Exemplary crystalline berberine ketone adducts disclosed herein for reaction crystallization include one or more of berberine ketone adducts wherein $R^1$ is H and $R^2$ is methyl, ethyl, phenyl, isopropyl, isobutyl, or $R^1R^2$=—$(CH_2)_4$—.

Reaction crystallization (or reactive crystallization or crystallization reaction) refers to the phenomenon comprising simultaneous reaction, mass transfer, crystal nucleation and growth, as well as possible secondary processes of aging, ripening, agglomeration and breakage. Reaction crystallization as disclosed herein is used in preparation of crystalline berberine ascorbate from a reaction mixture of one of berberine ketone adducts with the ascorbic acid. Surprisingly, the resulting crystalline berberine ascorbate directly from the reaction mixture has a high level of crystallinity and a high chemical purity profile.

Crystalline berberine ascorbate as disclosed herein can be prepared through various methods. Some specific methods for preparing a crystalline berberine ascorbate salt as disclosed herein include, but are not limited to, (a) isolation of crystalline solid of berberine ascorbate directly from the reaction slurry of the berberine ketone adduct and the ascorbic acid in non-aqueous organic solvents. (b) if water is used in the reaction, evaporation of the resulting reaction solution to obtain crystalline or hemi-crystalline, or amorphous solids. (c) recrystallization of berberine ascorbate. Large-scale manufacture can be achieved by one of these methods disclosed herein for potential commercial product development.

In the disclosed methods to prepare crystalline berberine ascorbate, a ratio between the berberine ketone adduct and the ascorbic acid from about 1:2 to about 2:1, preferably about 1:1.

In order to produce a high quality of crystalline berberine ascorbate from the reaction mixture, various factors, including solvents, reaction temperatures, reaction times and the starting material of berberine ketone adduct, were considered to achieve a robust reaction crystallization process.

The term "solvent" as used herein refers to any inorganic or organic solvent. Certain solvents can be a part of the crystalline salt disclosed herein. Solvents are useful in the disclosed method or article, product, or composition as reaction solvent or carrier solvent. Suitable solvents include, but are not limited to, lower alkyl alcohols, aliphatic and aromatic hydrocarbons, dialkyl ethers, dialkyl ketones, alkyl acetates, acetonitrile, chlorinated alkanes, dimethyl sulfoxide (DMSO), dimethylformamide (DMF), and aqueous solvents. Examples of solvents include, but are not limited to, methanol, ethanol, propanol, isopropanol and butanol, isobutanol, ethyl acetate, iso-propyl acetate, n-heptane, diethyl ether, tert-butyl methyl ether, acetone, dichloromethane, or water. The solvents used herein can be of a single solvent or a mixture of many different solvents. Crystalline berberine ascorbate Form A or Form B was prepared through reaction crystallization with selection of reaction different solvents. The solvents used in reaction crystallization to crystallize the anhydrous form, e.g. crystalline berberine ascorbate Form A, were ethanol, isopropanol, acetonitrile, tetrahydrofuran, ethyl acetate, or methyl tertiary-butyl ether. The hydrate form, e.g. crystalline ascorbate Form B, was obtained when reaction solvents contains water.

Reaction crystallization temperatures and times depend upon targeted crystalline form of berberine ascorbate that is to be crystallized, the concentration of the salt in solution, and the solvent system and the starting berberine ketone adduct which is used. At the room temperature or a lower temperature, the reaction does not proceed. At the elevated temperature above 50° C., the reaction starts to proceed and precipitate the desired crystalline berberine ascorbate salt. On the other hand, if the reaction temperature is too high and/or the reaction temperature is too long, the crystalline salt starts to decompose and generate chemical impurities. The preferred reaction time is about 0.5-2 hours with reaction temperature of 60-80° C., followed by stirring at the room temperature for 1-24 hours for crystalline berberine ascorbate to be completely precipitated out from the reaction mixture. The reaction crystallization process includes dissolving a berberine ketone adduct into the reaction solvent, completing the chemical reaction, and precipitating out the desire crystalline berberine ascorbate salt from the reaction mixture. In some exemplary methods, crystalline berberine ascorbate was obtained by a solid-solid conversion from a berberine ketone adduct to the crystalline salt at an elevated temperature. In some exemplary methods, crystalline berberine ascorbate was precipitated out from the reaction solution at an elevated temperature after a starting material of berberine ketone adduct was completely dissolved. In some exemplary methods, crystalline berberine ascorbate product started to precipitate after the reaction solution was cooled down to the room temperature. In some exemplary methods, crystalline berberine ascorbate product started to precipitate after concentrating the reaction solution by evaporation.

Reaction crystallization from reaction mixtures of various berberine ketone adducts with ascorbic acid produced similar yields of product as crystalline berberine ascorbate Form A, and reaction crystallization starting with crystalline berberine methyl phenyl ketone adduct provided a slightly better yield compared to other starting materials in a similar reaction condition.

Reaction crystallization may also be initiated and/or effected by way of standard techniques, for example with or without seeding with crystals of the appropriate crystalline salt of this disclosure.

The preparation method disclosed herein is a method of reaction crystallization to prepare crystalline berberine ascorbate Form A, the method comprises suspending one of berberine adducts of ketones, including acetone, methyl ethyl ketone (MEK), methyl phenyl ketone (MPHK), methyl isopropyl ketone (MIPK), methyl isobutyl ketone (MIBK) and cyclohexanone, in an organic solvent (including, but is not limited to, ethanol, isopropanol, acetonitrile, ethyl acetate, tetrahydrofuran, dichloromethane, tertbutyl methyl ether) to obtain a suspension; stirring the suspension in a temperature of about 50-80° C. for about 0.5 to 4 hours; cooling the suspension to room temperature; filtering, washing, and drying the resulted solid to obtain crystalline berberine ascorbate Form A.

The preparation method as disclosed herein is a method to prepare crystalline berberine ascorbate Form B, the method comprises suspending one of berberine adducts of ketones, including acetone, methyl ethyl ketone (MEK), methyl phenyl ketone (MPHK), methyl isopropyl ketone (MIPK), methyl isobutyl ketone (MIBK) and cyclohexanone, in the water or a combination of water with other organic solvent (including, but is not limited to, ethanol, isopropanol, acetonitrile, ethyl acetate, tetrahydrofuran) to obtain a suspension; stirring the suspension in a temperature of about 60-100° C. to obtain a brown solution. Cooling the solution to room temperature; concentrating the solution to precipitate the solid; filtering, washing, and drying the resulted solid to obtain crystalline berberine ascorbate Form B.

Crystalline berberine ascorbate Form A was also obtained from recrystallization of berberine ascorbate, e.g. by stirring solids of amorphous, crystalline Form B, crystalline Form C or crystalline Form D in an organic solvent at an elevated temperature, or by directly heating solids of Form D up to about 160° C. However, Form A obtained from recrystallization was only partially crystalline material and contained a significantly high level of chemical impurity.

Different solid forms comprising the same berberine ascorbate, including amorphous form, hemi-crystalline, Form C, Form D, or other crystalline forms, could be obtained by recrystallization of berberine ascorbate. Recrystallization methods described herein includes the methods described in the Examples below, or by techniques including, but not limited to, heating, cooling, freeze drying, lyophilization, spray drying, quench cooling the melt, rapid solvent evaporation, slow solvent evaporation, solvent recrystallization, antisolvent addition, slurry recrystallization, crystallization from the melt, desolvation, recrystallization in confined spaces such as, e.g., in nanopores or capillaries, recrystallization on surfaces or templates such as, e.g., on polymers, recrystallization in the presence of additives, desolvation, dehydration, rapid cooling, slow cooling, exposure to solvent and/or water, drying, including, e.g., vacuum drying, vapor diffusion, sublimation, grinding (including, e.g., cryo-grinding and solvent-drop grinding), microwave-induced precipitation, sonication-induced precipitation, laser-induced precipitation and precipitation from a supercritical fluid. Unless otherwise specified, methods involving solvents described herein contemplate the use of any suitable common laboratory solvent, as known in the art. The particle size of resulting solid forms, which can vary, (e.g., from nanometer dimensions to millimeter dimensions), can be controlled, e.g.: by varying crystallization conditions (such as, e.g., the rate of crystallization and/or the crystallization solvent system); by altering spray drying operating parameters (including, e.g., feed solution concentration); and/or equipment design or by particle-size reduction techniques (e.g., grinding, milling, micronizing or sonication).

Crystalline berberine ascorbate Form C was prepared from evaporation of solutions of pure berberine ascorbate in methanol/water, ethanol/water, acetone/water, acetonitrile/water and tetrahydrofuran/water. Crystallin berberine ascorbate Form D was prepared from evaporation of solution of pure berberine ascorbate in water, Pharmaceutical Compositions A composition disclosed herein includes an effective amount or a therapeutically effective amount of a crystalline berberine ascorbate salt as disclosed herein.

As one skilled in the art will ascertain, an effective amount or an amount sufficient to treat (e.g. therapeutically effective amount) refers to the amount of a pharmaceutical composition administered to improve, inhibit, or ameliorate a condition of a subject, or a symptom of a disorder, in a clinically relevant manner. Any improvement in the subject is considered sufficient to achieve the treatment. Preferably, an amount sufficient to treat is an amount that prevents the occurrence or one or more symptoms of the diseases or conditions or is an amount that reduces the severity of, or the length of time during which a subject suffers from, one or more symptoms of the diseases or conditions.

By its "pharmaceutical composition", the crystalline berberine ascorbate as disclosed herein provides the therapeutically or biologically active agent for formulation into a suitable delivery means for administration to a subject. For the purposes of this disclosure, pharmaceutical compositions suitable for delivering the berberine as disclosed herein can include, e.g., tablets, gelcaps, capsules, pills, powders, granulates, suspensions, emulsions, solutions, gels, hydrogels, oral gels, pastes, eye drops, ointments, creams, plasters, drenches, delivery devices, suppositories, enemas, injectables, implants, sprays, or aerosols. Any of the aforementioned formulations can be prepared by well-known and accepted methods of art.

In an aspect, the pharmaceutical compositions disclosed herein comprise a crystalline berberine ascorbate as disclosed herein and a pharmaceutically acceptable carrier or excipient. The term "pharmaceutically acceptable" means approved by a regulatory agency of the Federal or a state government or listed in the U.S. Pharmacopeia or other generally recognized pharmacopeia for use in animals, and more particularly in humans.

Examples of suitable pharmaceutically acceptable carriers or excipients that can be used in said pharmaceutical compositions include, but are not limited to, sugars (e.g., lactose, glucose or sucrose), starches (e.g., corn starch or potato starch), cellulose or its derivatives (e.g., sodium carboxymethyl cellulose, ethyl cellulose or cellulose acetate), oils (e.g., peanut oil, cottonseed oil, safflower oil, sesame oil, olive oil, corn oil or soybean oil), glycols (e.g., propylene glycol), buffering agents (e.g., magnesium hydroxide or aluminum hydroxide), agar, alginic acid, powdered tragacanth, malt, gelatin, talc, cocoa butter, pyrogen-free water, isotonic saline, Ringer's solution, ethanol, phosphate buffer solutions, lubricants, coloring agents, releasing agents, coating agents, sweetening, flavoring or perfuming agents, preservatives, or antioxidants.

The term "excipient" refers to additives and stabilizers typically employed in the art (all of which are termed "excipients"), including for example, buffering agents, stabilizing agents, preservatives, isotonifiers, non-ionic detergents, antioxidants and/or other miscellaneous additives. Stabilizers refer to a broad category of excipients which can range in function from a bulking agent to an additive which solubilizes the disclosed salts or helps to prevent denaturation of the same. Additional conventional excipients include, for example, fillers (e.g., starch), chelating agents (e.g., EDTA), antioxidants (e.g., ascorbic acid, methionine, vitamin E) and cosolvents.

The term "carrier" refers to a diluent, adjuvant, excipient, or vehicle with which the pharmaceutical composition is administered. Such pharmaceutical carriers are illustratively sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions are optionally employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, also contains wetting or emulsifying agents, or pH buffering agents. These compositions optionally take the form of solutions, suspensions, emulsion, tablets, pills, capsules, powders, sustained release formulations and the like. The composition is optionally formulated as a suppository, with traditional binders and carriers such as triglycerides. Oral formulation illustratively includes standard carriers such as pharmaceutical grades of mannitol, lactose, starch, magnesium stearate, sodium saccharine, cellulose, magnesium carbonate, etc.

In an aspect, pharmaceutical compositions according to the disclosure may be formulated to release the composition immediately upon administration (e.g., targeted delivery) or at any predetermined time period after administration using controlled or extended release formulations. Administration of the pharmaceutical composition in controlled or extended release formulations is useful where the composition, either alone or in combination, has (i) a narrow therapeutic index; (ii) a narrow absorption window in the gastro-intestinal tract; or (iii) a short biological half-life, so that frequent dosing during a day is required in order to sustain a therapeutic level. One skilled in the art will ascertain compositions for controlled or extended release of the pharmaceutical composition. In an aspect, controlled release can be obtained by controlled release compositions and coatings which are known to those of skill in the art.

Methods of Use/Treatment

A crystalline berberine ascorbate as disclosed herein is employed in methods of therapeutic or prophylactic treatment of a subject, which may be referred to as an animal, including a human, to treat or prevent gastrointestinal infections or other conditions. As referred to herein, gastrointestinal infections or conditions include any disease state or condition can be or can be treated or prevented by berberine chloride salt or other medications.

By "treating" is meant administering a crystalline berberine ascorbate as disclosed herein for prophylactic and/or therapeutic purposes. Prophylactic treatment may be administered, for example, to a subject who is not yet ill, but who is susceptible to, or otherwise at risk of, a particular disorder, e.g., gastrointestinal infections or other conditions. Prophylactic treatment reduces the likelihood of a subject to develop cardiovascular diseases or conditions. Therapeutic treatment may be administered, for example, to a subject already suffering from a disorder to improve or stabilize the subject's condition. Thus, in the claims and embodiments described herein, treating is the administration to a subject either for therapeutic or prophylactic purposes.

The methods of treatment disclosed herein may be performed alone or in conjunction with another treatment. The methods of treatment may further be combined with other therapeutic agents, including for example, another antibacterial agent.

Crystalline Berberine Ketone Adducts and Method of Preparation

Berberine ketone adducts as disclosed herein are key starting materials for preparing crystalline berberine ascorbate. An exemplary reaction crystallization scheme to prepare crystalline berberine ascorbate is shown below.

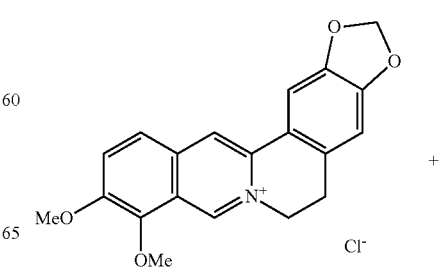

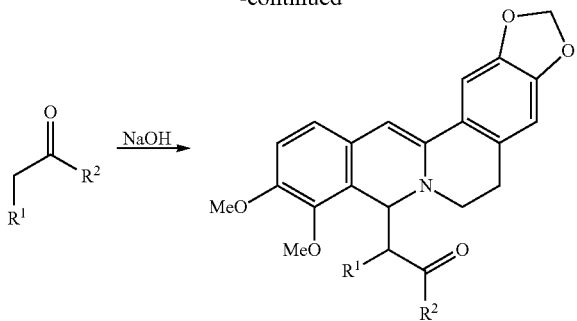

wherein $R^1$ is H, or a $C_1$-$C_5$ alkyl group and $R^2$ is an $C_1$-$C_{10}$ alkyl group or the aryl group or substituted group thereof; or $R^1R^2$ is methylene bridge group, $C_2$-$C_6$ alkylene group, substituted or unsubstituted group thereof.

Exemplary crystalline berberine ketone adducts disclosed herein for reaction crystallization include one or more of berberine ketone adducts wherein $R^1$ is H and $R^2$ is methyl, ethyl, phenyl, isopropyl, isobutyl, or $R^1R^2$=—$(CH_2)_4$—.

A berberine acetone adduct was previously prepared from reaction of berberine chloride or berberine sulphate with the ketone in a basic sodium hydroxide solution with a refluxing temperature of 80-100° C. Other berberine ketone adducts, including berberine methyl ethyl ketone adduct and berberine methyl phenyl ketone adduct, were prepared under the same reaction condition. (JP 49001599 A Jan. 1974 Noguchi et al.) Various literatures disclosed a similar reaction condition of preparation of berberine ketone adducts, specially berberine acetone adduct, by using the water as the solvent and a refluxing temperature, There was no report to disclose about crystallinity or crystalline forms this reaction condition.

It was known that berberine was chemically unstable in a basic solution, especially in an elevated temperature. Various chemical degradants generated from such a reaction condition not only decreased chemical impurity profile but also inhibited crystal nucleation and/or crystal growth. As a result, berberine ketone adduct obtained from such a reaction condition usually generated amorphous or hemi-crystalline material with a sub-optimal chemical purity profile. The chemical purity profile of berberine ketone adducts from this condition was not suitable for reaction crystallization process disclosed herein to produce crystalline berberine ascorbate with an optimal chemical purity profile.

As disclosed herein, an improved reaction condition was investigated in crystallizing and purifying berberine acetone adduct and other ketone adducts. One of the key improvements of the new reaction condition is to select appropriate solvents to allow the reaction to occur at the room temperature to avoid decomposition of berberine, so that crystalline berberine ketone adducts with suitable chemical purity profile could be obtained. Instead of using water as a single solvent, a mixture of water and the organic solvent is needed to ensure dissolving the starting berberine salt and reacting with ketone in the room temperature. It is also important to choose a solvent system to allow crystalline berberine ketone adduct to be precipitated out from the reaction mixture. Although ketones themselves were used as organic solvents for various chemical reaction, ketones in this reaction usually served as antisolvent to precipitate the starting material, e.g. berberine chloride. Furthermore, some ketones, e.g. methyl phenyl ketone and cyclohexanone, are not miscible with water and two layers were observed in the reaction when only water was used as a solvent. In some exemplary experiments, the additional organic solvent serves as a solvent to dissolve berberine chloride into reaction mixture. In some other exemplary experiments, the additional organic solvent serves as a solvent and an agent to improve miscibility of water with a ketone. Some organic solvents, e.g. acetonitrile (ACN), tetrahydrofuran (THF), dichloromethane (DCM), ethyl acetate (EtOAc), tertiary butyl methyl ester (TBME), are not able to improve the solubility of berberine chloride and/or the miscibility between water and the ketone so that the reaction won't occur or be completed at the room temperature. On the other hand, some other solvents, e.g. dimethylformamide (DMF) and dimethyl sulfoxide (DMSO), significantly improves the solubility and the miscibility, however, it is very difficult to isolate berberine ketone adducts from reaction mixtures because berberine ketone adducts also have a high solubility in DMF and DMSO. Crystalline berberine ketone adducts do not precipitate out without removing DMF or DMSO solvents with high boiling points. Alcohol solvents, including methanol (MeOH), ethanol (EtOH) and isopropanol (iPrOH), were selected as both a solvent and a miscibility agent to allow chemical reaction and crystallization to occur in the room temperature. A mixture of solvents of water and alcohol, preferred as methanol, was used to dissolve berberine chloride in a sodium hydroxide aqueous solution, followed by addition of the ketone. Such a modified reaction condition allowed reaction of berberine with ketones in the room temperature and precipitation of crystalline berberine ketone adducts at the same time.

By using this modified condition, a crystalline berberine acetone adduct was obtained, and a crystalline form of berberine acetone adduct was disclosed for the first time (CN 111205285 pending/2020 Xie et al.). Disclosed herein is furtherly optimizing the ratio of alcohol and water for reaction solvents to achieve improved yield, crystallinity, or chemical purity profile for berberine acetone adduct and other ketone adducts.

The appropriate ratio of methanol and water is needed for better production of berberine ketone adducts. A higher ratio of methanol and water benefits dissolving berberine chloride in the reaction mixture but has a disadvantage for crystalline berberine ketone adducts to be precipitated out from the reaction mixture, resulting a lower yield. A lower ratio of methanol and water could produce more berberine ketone adduct but may scarify the chemical impurity. In fact, the starting material berberine chloride could be precipitated out if too much water is added into the reaction mixture at the room temperature. The optimized ration of methanol and water was employed in preparation of various crystalline berberine ketone adducts.

Crystalline berberine methyl ethyl ketone adduct and crystalline berberine methyl phenyl ketone adduct were obtained by using the reaction condition with an optimized methanol/water ratio and disclosed herein. New berberine ketone adducts, including berberine methyl isopropyl ketone adduct, berberine isobutyl ketone adduct and berberine cyclohexanone adduct, were also obtained as crystalline materials and disclosed herein.

In another respect, disclosed herein is a berberine ketone adduct, wherein the adduct is a crystalline solid of at least about 75% crystalline material; wherein the berberine ketone adduct has a following structure:

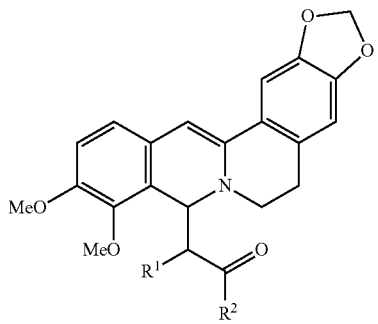

wherein $R^1$ is H, or a $C_1$-$C_5$ alkyl group and $R^2$ is an $C_1$-$C_{10}$ alkyl group or the aryl group or substituted group thereof; or $R^1R^2$ is methylene bridge group, $C_2$-$C_6$ alkylene group, substituted or unsubstituted group thereof.

Exemplary crystalline berberine ketone adducts disclosed herein for reaction crystallization include one or more of berberine ketone adducts wherein $R^1$ is H and $R^2$ is methyl, ethyl, phenyl, isopropyl, isobutyl, or $R^1R^2$=—$(CH_2)_4$—.

A highly crystalline material of berberine acetone adduct was prepared and a melting/decomposition point of about 168° C. was observed. Berberine acetone adduct is a chiral molecule with R- and S-opposite enantiomers and could exist in various crystal types, including conglomerate, racemic compound, solid solution. (Reference: Crystal Growth & Design, 2010, 10(4), 1808-1812.) As a chiral molecule, one of crystalline berberine ketone adducts in this disclosure could crystallize as conglomerate crystals, in which only single enantiomeric configuration, either R- or S-, exists in each single crystal. The adduct could also crystallize as racemic crystals, in which pairs of R- and S-opposite enantiomers co-exist in each single crystal. In addition, the adduct could crystallize as solid solution crystals, in which R- and S-enantiomers randomly exist in each single crystal. Crystalline berberine ketone adducts could consist of a single type of the three crystal types of conglomerate, racemic compound and solid solutions, or a physical mixture of two or three crystal types in bulk crystalline materials. Single crystal structure of the berberine acetone adduct was determined and disclosed herein, The crystalline berberine acetone adduct crystallizes in a non-symmetric orthorhombic $P2_12_12_1$ space group, confirming that the crystalline berberine acetone adduct prepared herein belongs to conglomerate crystals, in which only single enantiomeric configuration, either R- or S-, exists in each single crystal.

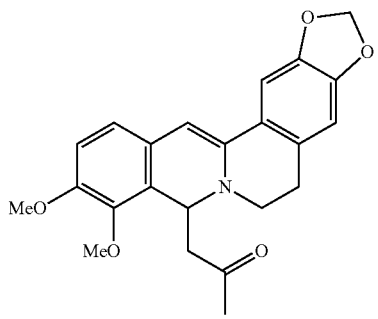 [SMILES: COc1ccc2c(c1OC)C(CC(C)=O)N1CCc3cc4c(cc3C1=C2)OCO4]

Two other crystalline berberine ketone adducts, berberine methyl ethyl ketone adduct and the methyl phenyl ketone adduct, were prepared by using improved reaction conditions. Remarkably, crystalline solids were obtained directly from reaction mixtures, yielding crystalline berberine methyl ethyl ketone adduct with a melting point of about 130° C. and crystalline methyl phenyl ketone adduct with a melting point of about 140° C.

In one embodiment, crystalline berberine methyl ethyl ketone adduct disclosed herein with the following structure is an anhydrous form and is characterized by an XRPD pattern comprising one or more peaks expressed as 2θ±0.2° of about 10.9°, about 15.1°, about 17.1°, about 17.8°, about 20.2°, about 21.6°, about 21.8°, about 22.3°, about 25.6°, and about 26.0°.

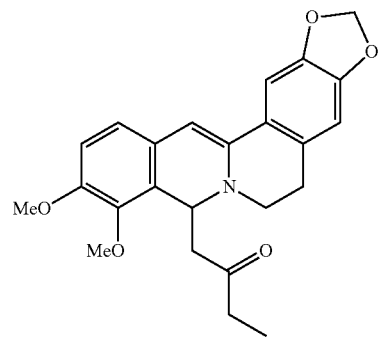 [SMILES: CCC(=O)CC1c2c(ccc(OC)c2OC)C=C2c3cc4c(cc3CCN21)OCO4]

In another embodiment, crystalline berberine methyl phenyl ketone adduct disclosed herein with the following structure is an anhydrous form and is characterized by an XRPD pattern comprising one or more peaks expressed as 2θ±0.2° of about 11.8°, about 12.3°, about 12.9°, about 15.1°, about 16.8°, about 17.5°, about 18.3°, about 19.3°, about 21.3°, and about 26.0°.

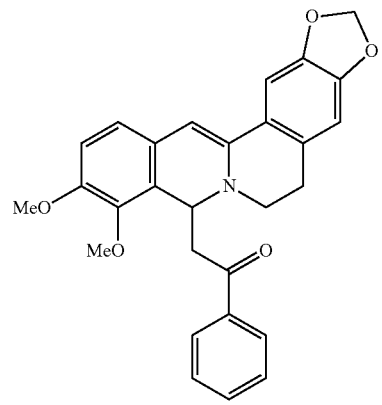 [SMILES: COc1ccc2c(c1OC)C(CC(=O)c1ccccc1)N1CCc3cc4c(cc3C1=C2)OCO4]

Two new compounds, berberine methyl isopropyl ketone adduct and methyl isobutyl ketone adduct, were prepared and disclosed herein. Both compounds, berberine methyl isopropyl ketone adduct with a melting point of about 85° C. and methyl isobutyl ketone adduct with a melting point of about 82° C., precipitated out as a high crystalline material without additional recrystallization by using modified reaction condition as disclosed herein. Such surprising low melting points in these two adducts made it problematic if not impossible to precipitate and crystallize out in a refluxing temperature of water/ketone of about 80-100° C., which was needed in previously published reaction conditions. Single crystal structure determination reveals that crystalline berberine isopropyl ketone adduct crystallizes in a non-symmetric monoclinic P2₁ space group, indicating the new crystalline berberine methyl isopropyl ketone adduct belongs to conglomerate crystals, in which only a single enantiomeric configuration, either R- or S-, exists in each single crystal.

In one embodiment, a new compound of berberine methyl isopropyl ketone adduct disclosed herein is prepared from the modified condition at the room temperature. The crystalline form of berberine methyl isopropyl ketone adduct disclosed herein with the following structure is an anhydrous form and is characterized by an XRPD pattern comprising one or more peaks expressed as 2θ±0.2° of about 9.9°, about 14.7°, about 16.7°, about 17.2°, about 19.8°, about 20.1°, about 21.4°, about 21.8°, about 25.0°, and about 25.3°.

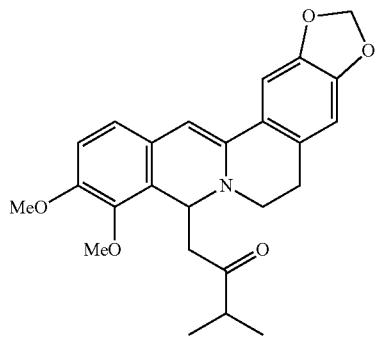 [SMILES: COc1ccc2c(c1OC)C(CC(=O)C(C)C)N1CCc3cc4c(cc3C1=C2)OCO4]

In another embodiment, a new compound of berberine methyl isobutyl ketone adduct disclosed herein is prepared from the modified condition at the room temperature. The crystalline form of berberine methyl isobutyl ketone adduct disclosed herein with the following structure is an anhydrous form and is characterized by an XRPD pattern comprising one or more peaks expressed as 2θ±0.2° of about 5.7°, about 9.3°, about 14.7°, about 16.4°, about 17.1°, about 18.8°, about 20.0°, about 20.9°, about 22.4°, and about 25.0°.

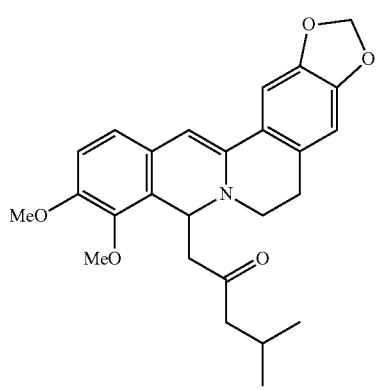 [SMILES: COc1ccc2c(c1OC)C(CC(=O)CC(C)C)N1CCc3cc4c(cc3C1=C2)OCO4]

Another new compound, berberine cyclohexanone adduct, was also prepared and disclosed herein. A berberine cyclohexanone adduct disclosed herein has the following structures.

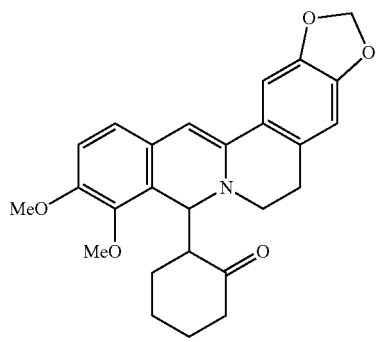 [SMILES: COc1ccc2c(c1OC)C(C1CCCCC1=O)N1CCc3cc4c(cc3C1=C2)OCO4]

Berberine cyclohexanone adduct represents the first berberine ketone adduct containing a secondary carbon attached to the carbonyl group, resulting possible R/R, S/S, R/S and S/R four diastereomers in following structures related to the two chiral carbon centers formed during the reaction. Surprisingly, reaction under an optimized mild condition, specifically at the room temperature, as disclosed herein yielded a highly crystalline berberine cyclohexanone adduct with a melting point of about 169° C. Crystalline berberine cyclohexanone adduct could contain one, two, three or all the four diastereomers. Each crystal of berberine cyclohexanone adduct could contain only one enantiomer of the four diastereomers as a conglomerate crystal, e.g. R/R, S/S, R/S or S/R; or only pairs of two opposite enantiomers as racemic compound, either pairs of R/R and S/S, or pairs of R/S and S/R; or all four diastereomers, R/R, S/S, R/S and S/R, in various content ratios. The bulk crystalline material of berberine cyclohexanone could contain any combinations of physical mixtures of single crystals.

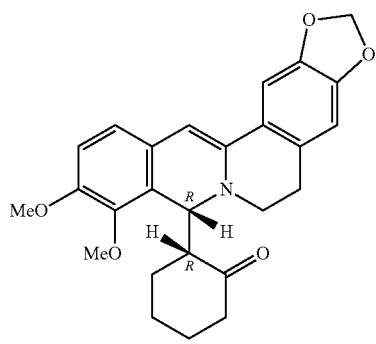

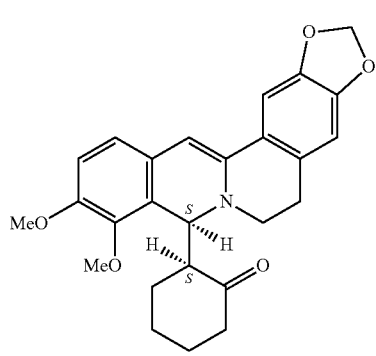

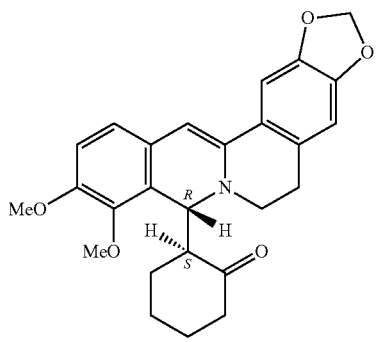

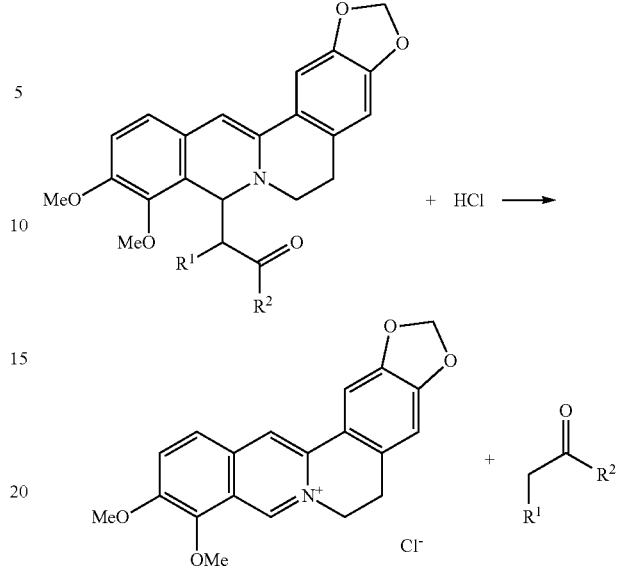

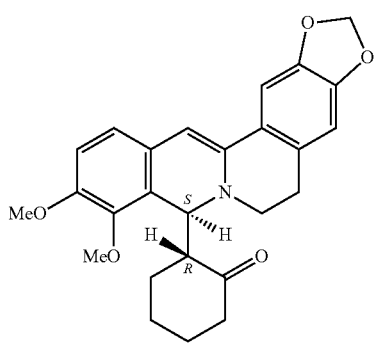

In another embodiment, a new compound of the berberine cyclohexanone adduct disclosed herein is prepared from the modified condition at the room temperature. The crystalline berberine cyclohexanone adduct disclosed herein with the following structure is an anhydrous form and is characterized by an XRPD pattern comprising one or more peaks expressed as 2θ±0.2° of about 13.0°, about 14.7°, about 16.5°, about 16.8°, about 19.3°, about 20.1°, about 21.2°, about 22.9°, about 23.9°, and about 26.2°.

Chemical purity of the berberine ketone adduct as a staring material plays a key role to obtain crystalline berberine ascorbate with an optimal chemical purity profile. In some exemplary results, crystalline berberine ketone adduct obtained directly from reaction mixture of berberine chloride and the ketone was suitable to be used as the starting material in reaction crystallization for preparation of crystalline berberine ascorbate. In some other exemplary results, the berberine ketone adduct was not pure enough to be used as the starting material, and an additional recrystallization process was required to obtain purer crystalline berberine ketone adduct. In some other exemplary results, the berberine ketone adduct was not pure enough to be used as the starting material, and the berberine ketone adduct needed to be converted back to crystalline berberine chloride with a better chemical purity profile than that of the original berberine chloride crude. An exemplary reaction scheme to convert berberine ketone adducts to berberine chloride is shown below.

wherein $R^1$ is H and $R^2$ is the alkyl group or the aryl group includes methyl, ethyl, isopropyl, isobutyl, phenyl or substituted group thereof; wherein $R^1R^2$ is methylene bridge group, including $R^1R^2$=—$(CH_2)_4$—, substituted or unsubstituted group thereof.

As disclosed herein, after transferring from berberine chloride crude to one of crystalline berberine ketone adducts, the berberine ketone adduct reacts with hydrochloric acid to produce berberine chloride salt with a better chemical purity profile to be used as starting. Purified berberine chloride was obtained by a general procedure from one of berberine ketone adducts. 0.10 mmol of one of berberine ketone adducts, was suspended in 1.1 ml of 0.10 N hydrochloric acid aqueous solution (0.11 mmol). The suspension was heated to about 80° C. and stirred for about 30 minutes. In suspension of berberine acetone adduct, berberine methyl phenyl ketone adduct or berberine cyclohexanone adduct, the pale-yellow or the yellow solid was converted to a yellow solid; In suspension of berberine methyl isopropyl ketone adduct or berberine methyl isobutyl ketone adduct, the pale-yellow solid was dissolved in the solution, and then a yellow solid started to precipitate out. In suspension of berberine methyl ethyl ketone adduct, the pale-yellow solid was dissolved and a clear yellow solution was obtained. A homogenous slurry was obtained after the suspension or the solution was cooled down to the room temperature and stirred for about 10 hours. The yellow solid was collected by filtration, washed with small amount of water, and then dried in the air. Crystalline berberine chloride tetrahydrate was obtained.

Surprisingly, product yields for the preparation are different when using various berberine ketone adducts. Specially, the product yield increased to >80% when starting with new crystalline berberine isobutyl ketone adduct from <50% when starting with the known crystalline berberine acetone adduct by using the same reaction condition.

Remarkably, by using berberine methyl ethyl ketone adduct, berberine methyl isopropyl ketone adduct, berberine methyl isobutyl ketone adduct, it is easier to monitor the reaction endpoint by virtually observation of forming a clear solution prior to precipitating berberine chloride, compared to using the known crystalline berberine acetone adduct as starting material, in which solid-to-solid conversion from berberine acetone adduct to berberine chloride was observed.

The purified berberine chloride was used as new starting material to prepare crystalline berberine ketone adducts with acceptable chemical purity profile for preparing crystalline berberine ascorbate. This process could be also used in preparation of purified berberine chloride salt or other salts by converting berberine crude into one of berberine ketone adducts, followed by converting to the desired berberine chloride salt or other salts, to achieve a higher chemical purify to be used in pharmaceutical or dietary products.

The foregoing summary is illustrative only and is not intended to be in any way limiting. In addition to the illustrative aspects, embodiments, and features described above, further aspects, embodiments, and features will become apparent by reference to the drawings and the following detailed description.

All publications, patent applications, issued patents, and other documents referred to in this specification are indicative of the level of ordinary skill in the art to which this disclosure pertains and are herein incorporated by reference to the same extent as if each individual publication or patent application was specifically and individually indicated as incorporated by reference. Definitions that are contained in text incorporated by reference are excluded to the extent that they contradict definitions in this disclosure.

The present disclosure is further illustrated by the following examples, which should not be considered as limiting in any way.

EXAMPLES

Embodiments of the present disclosure are further defined in the following non-limiting Examples. It should be understood that these Examples, while indicating certain embodiments of the disclosure, are given by way of illustration only. From the above discussion and these Examples, one skilled in the art can ascertain the essential characteristics of this disclosure, and without departing from the spirit and scope thereof, can make various changes and modifications of the embodiments of the disclosure to adapt it to various usages and conditions. Thus, various modifications of the embodiments of the disclosure, in addition to those shown and described herein, will be apparent to those skilled in the art from the foregoing description. Such modifications are also intended to fall within the scope of the appended claims.

Chemicals and Analytic Method

Chemicals

All the compounds, including berberine chloride, berberine hemisulfate, and the ketone solvents used in the experiments, were purchased from Sigma-Aldrich and used without further purification.

Analytical Methods

Nuclear Magnetic Resonance (NMR) Spectroscopy

In general, the structures of end-products of the salt were confirmed by nuclear magnetic resonance (NMR) spectroscopy. Proton magnetic resonance spectra were taken using a Bruker Advance 500 (500 MHz) and NMR chemical shift values were given in ppm. Proton NMR measurements were taken at ambient temperature unless otherwise specified; the following abbreviations have been used for characterizing NMR peaks: s, singlet; d, doublet; t, triplet; q, quartet; m, multiplet; dd, doublet of doublets; ddd, doublet of doublet of doublet; dt, doublet of triplets; bs, broad signal. The chemical shifts (δ) of the NMR peak are reported in parts per million (ppm) downfield of tetramethylsilane (TMS) and referenced to the respective residual un-deuterated solvent peak as follows: $CDCl_3$=7.26 ppm, MeOH-$d_4$=3.31 ppm for $^1$H-NMR. Apparent coupling constants (J) are reported in Hz.

X-Ray Powder Diffraction (XRPD) Analysis

In general, the crystalline forms of the salts were analyzed by X-ray powder diffraction (XRPD), which provides a fingerprint of a crystalline form. XRPD analysis was performed using a Bruker D8 diffractometer by Bruker AXS Inc™ (Madison, Wis.). The XRPD spectra were obtained by mounting a sample (approximately 10 mg) of the material for analysis on a single silicon crystal wafer mount (e.g., a Bruker silicon zero background X-ray diffraction sample holder) and spreading out the sample into a thin layer with the aid of a microscope slide. The sample was spun at 30 revolutions per minute (to improve counting statistics) and irradiated with X-rays generated by a copper long-fine focus tube operated at 40 kV and 40 mA with a wavelength of 1.5406 angstroms (e.g., about 1.54 angstroms). The sample was exposed for 1 second per 0.02 degree 2-theta increment (continuous scan mode) over the range 5 degrees to 40 degrees 2-theta in theta-theta mode. The running time was ~15 min for such a measurement.

XRPD 2θ values may vary with a reasonable range, e.g., in the range ±0.2° and the XRPD intensities may vary when measured for essentially the same crystalline form for a variety of reasons including, for example, preferred orientation.

Differential Scanning Calorimetry (DSC) Analysis

DSC analysis was performed on samples prepared according to standard methods using a Q SERIES™ Q1000 DSC calorimeter available from TA INSTRUMENTS® (New Castle, Del.). A sample (approximately 2 mg) was weighed into an aluminum sample pan and transferred to the DSC. The instrument was purged with nitrogen at 50 mL/min and data collected between 22° C. and 300° C., using a dynamic heating rate of 10° C./minute. Thermal data was analyzed using standard software, e.g., Universal Analysis v.4.5A from TA INSTRUMENTS®.

Thermogravimetry Analysis (TGA)

TGA was performed on samples prepared according to standard methods using a Q SERIES™ Q5000 thermogravimetry analyzer available from TA Instruments INSTRUMENTS® (New Castle, Del.). A sample (approximately 5 mg) was placed into an aluminum sample pan and transferred to the TGA furnace. The instrument was purged with nitrogen at 50 mL/min and data collected between 25° C. and 300° C., using a dynamic heating rate of 10° C./minute. Thermal data was analyzed using standard software, e.g., Universal Analysis v.4.5A from TA INSTRUMENTS®.

Example 1

Preparation and Characterization of an Exemplary Crystalline Berberine Ascorbate Form A Method 1. Preparation from Berberine Acetone Adduct A mixture of 79 mg of berberine acetone adduct (0.20 mmol) and 36 mg of L-ascorbic acid (0.20 mmol) was suspended in 4.0 ml of absolute ethanol. The suspension was heated and stirred at about 75° C. The yellow solid started to dissolve in about 10 minutes and a cloudy-like yellow solid precipitated at the same time. A homogenous slurry was obtained after stirring at about 75° C. for about 30 minutes. The slurry was cooled down to the room temperature and stirred for 1 hour. The yellow solid was collected by filtration, washed with small amount of EtOH, and then dried in the air. 62 mg of crystalline berberine ascorbate Form A was obtained (61% yield with >98.0% purity based on NMR).

The proton NMR spectrum of crystalline berberine ascorbate Form A in $CD_3OD$, shown in FIG. 1, indicates an about 1:1 ratio of the berberine and the ascorbate for the crystalline ascorbate salt. $^1H$ NMR (500 MHz, METHANOL-d4) δ ppm 3.57-3.74 (m, 2H) 3.78-3.91 (m, 1H) 4.06-4.16 (m, 3H) 4.17-4.25 (m, 3H) 4.26-4.39 (m, 1H) 4.78-4.89 (m, 6H) 4.90-5.01 (m, 2H) 6.02-6.20 (m, 2H) 6.91-7.05 (m, 1H) 7.57-7.73 (m, 1H) 7.92-8.05 (m, 1H) 8.06-8.20 (m, 1H) 8.64-8.78 (m, 1H) 9.68-9.85 (m, 1H).

Figure 2:
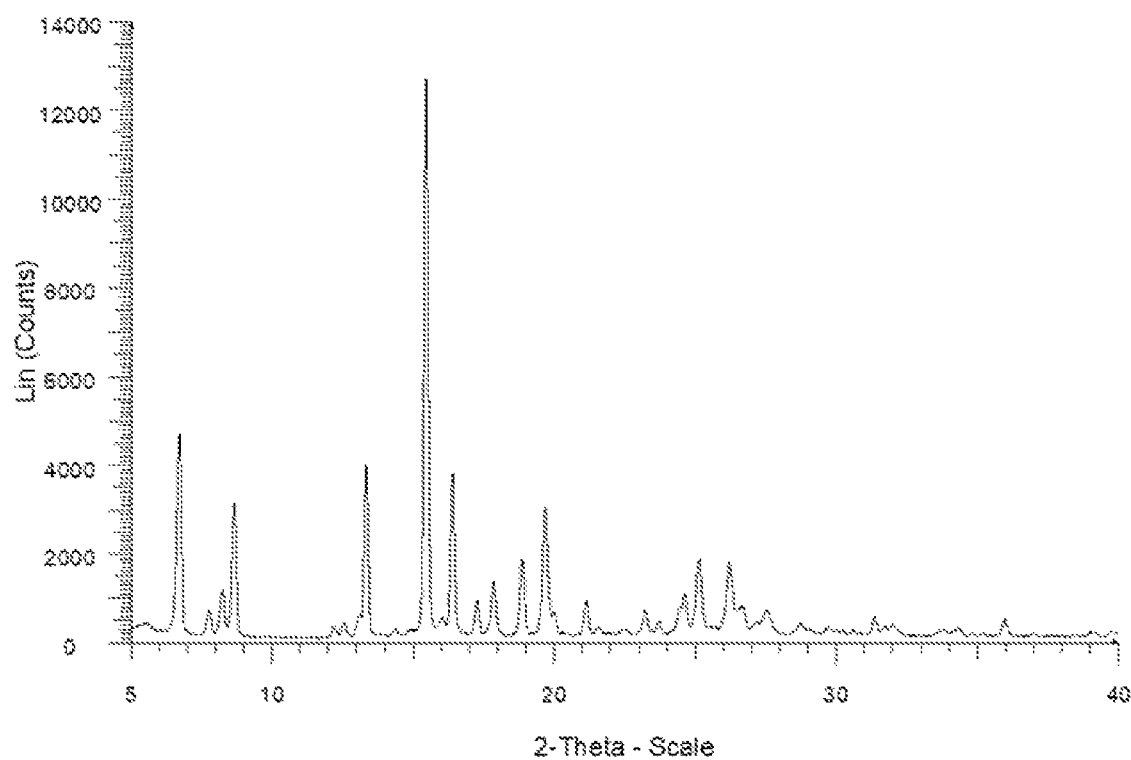
FIG. 2 shows the powder X-ray diffraction pattern of crystalline berberine ascorbate Form A.

Crystalline berberine ascorbate Form A was analyzed by XRPD. The key peaks from the XRPD pattern are tabulated in Table 1 and the XRPD pattern is shown in FIG. 2.

TABLE 1

XRPD Peaks for Berberine Ascorbate Form A

| Angle (2θ ± 0.2°) | Intensity (%) |
|---|---|
| 15.5 | 100.0 |
| 6.7 | 36.8 |
| 13.3 | 31.4 |
| 16.4 | 30.0 |
| 8.6 | 24.7 |
| 19.7 | 23.8 |
| 18.9 | 14.8 |
| 25.1 | 14.7 |
| 26.2 | 14.3 |
| 17.8 | 10.7 |

Figure 3:
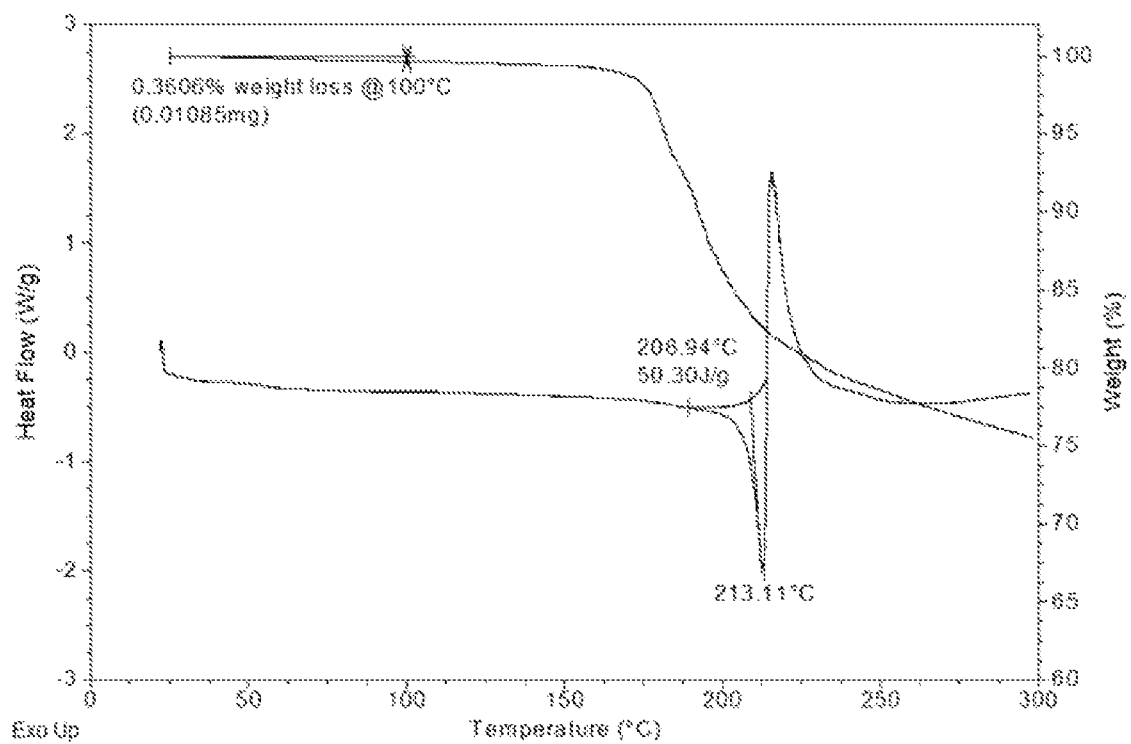
FIG. 3 shows the DSC/TGA diagrams of crystalline the berberine ascorbate Form A.

Crystalline berberine ascorbate Form A was also analyzed by the thermal analysis techniques. DSC analysis indicates that Form A has an endotherm event of melting and decomposition with an onset at about 209° C. and a peak at about 213° C. TGA indicates that Form A exhibits a mass loss of 0.4% upon heating from about 25° C. to about 100° C. A representative DSC/TGA thermogram of crystalline berberine ascorbate Form A is shown in FIG. 3.

Method 2. Preparation from Berberine Methyl Ethyl Ketone Adduct A mixture of 41 mg of berberine methyl ethyl ketone adduct (0.10 mmol) and 18 mg of L-ascorbic acid (0.10 mmol) was suspended in 2.0 ml of absolute ethanol. The suspension was heated and stirred at about 75° C. A yellow solution was obtained in about 10 minutes. Yellow solid started to precipitate, and a homogenous slurry was obtained in about 30 minutes. The slurry was cooled down to the room temperature and stirred for about 1 hour. The yellow solid was collected by filtration, washed with small amount of EtOH, and then dried in the air. 31 mg of crystalline berberine ascorbate Form A was obtained (61% yield).

Method 3. Preparation from Berberine Methyl Phenyl Ketone Adduct

A mixture of 91 mg of berberine methyl phenyl adduct (0.20 mmol) and 36 mg of L-ascorbic acid (0.20 mmol) was suspended in 4.0 ml of absolute ethanol. The suspension was heated and stirred at about 75° C. The yellow solid started to dissolve, and a yellow solution was obtained in about 10 minutes and a cloudy-like yellow solid precipitated at the same time. The yellow solid started to precipitate, and a homogenous slurry was obtained after stirring at about 75° C. for about 30 minutes. The slurry was cooled down to the room temperature and stirred for about 1 hour. The yellow solid was collected by filtration, washed with small amount of EtOH, and then dried in the air. 72 mg of crystalline berberine ascorbate Form A was obtained (70% yield).

Method 4. Preparation from Berberine Methyl Isopropyl Ketone Adduct

A mixture of 84 mg of berberine methyl isopropyl ketone adduct (0.20 mmol) and 36 mg of L-ascorbic acid (0.20 mmol) was suspended in 4.0 ml of absolute ethanol. The suspension was heated and stirred at about 75° C. A yellow solution was obtained in about 10 minutes. The clear solution was stirred at about 75° C. for about 30 minutes, and yellow solid started to precipitate after cooling down to the room temperature. The slurry was stirred at the room temperature for about 1 day. The yellow solid was collected by filtration, washed with small amount of EtOH, and then dried in the air. 66 mg of crystalline berberine ascorbate Form A was obtained (65% yield).

Method 5. Preparation from Berberine Methyl Isobutyl Ketone Adduct

A mixture of 44 mg of berberine methyl isobutyl ketone adduct (0.10 mmol) and 18 mg of L-ascorbic acid (0.10 mmol) was suspended in 2.0 ml of absolute ethanol. The suspension was heated and stirred at about 75° C. A yellow solution was obtained in about 10 minutes, and yellow solid started to precipitate. A homogenous slurry was obtained in about 30 minutes. The slurry was cooled down to the room temperature and stirred for about 1 hour. The yellow solid was collected by filtration, washed with small amount of EtOH, and then dried in the air. 31 mg of crystalline berberine ascorbate Form A was obtained (61% yield).

Method 6. Preparation from Berberine Cyclohexanone Adduct

A mixture of 43 mg of berberine cyclohexanone adduct (0.10 mmol) and 18 mg of L-ascorbic acid (0.10 mmol) was suspended in 2.0 ml of absolute ethanol. The suspension was heated and stirred at about 75° C. The solid started to dissolve about 10 minutes and a yellow solid started to precipitate at the same time. A homogenous slurry was obtained in about 30 minutes. The slurry was cooled down to the room temperature and stirred for about 1 hour. The yellow solid was collected by filtration, washed with small amount of EtOH, and then dried in the air. 30 mg of crystalline berberine ascorbate Form A was obtained (60% yield).

Example 2

Preparation and Characterization of an Exemplary Crystalline Berberine Ascorbate Form B A mixture of 40.1 mg of berberine acetone adduct (0.10 mmol) and 17.6 mg of L-ascorbic acid (0.10 mmol) was suspended in 2.0 ml of water. The suspension was heated and stirred at about 80° C. A brown solution was obtained in about 10 minutes. The clear solution was stirred for about 1 hours and then cooled down to the room temperature. The brown solution was concentrated and dried be evaporation. A yellow solid was obtained and collected. 39.0 mg of crystalline berberine ascorbate Form B was obtained (76% yield).

Figure 4:
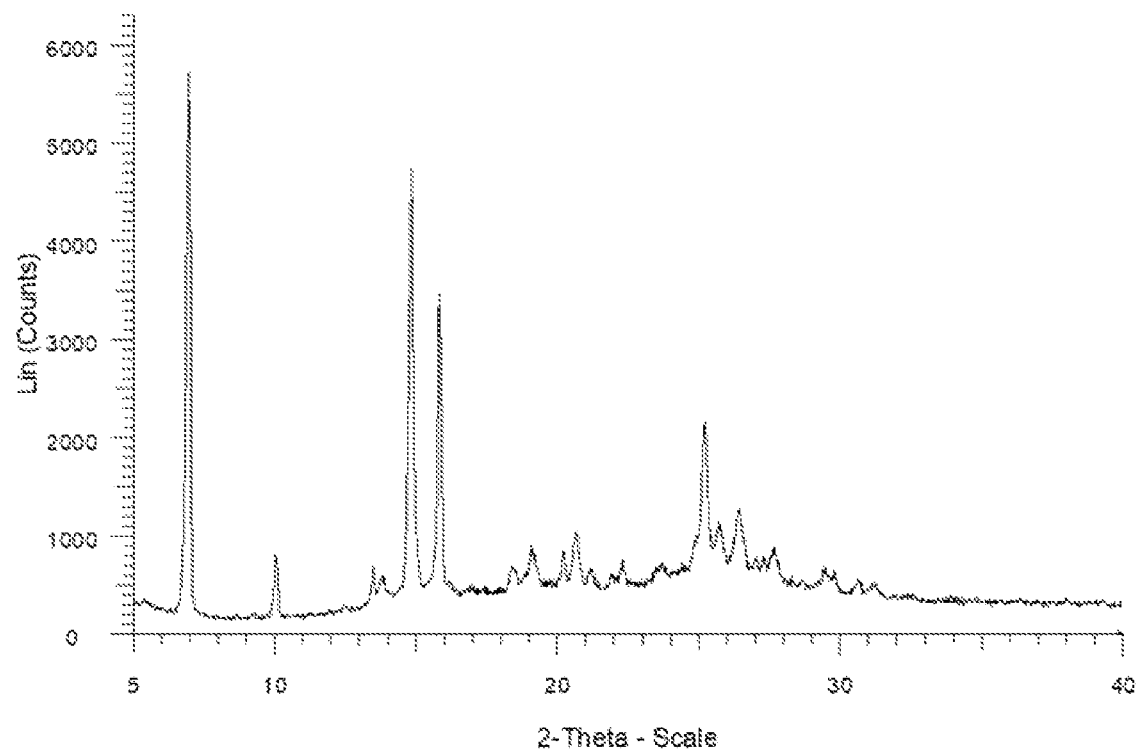
FIG. 4 shows the powder X-ray diffraction pattern of crystalline berberine ascorbate Form B.

Crystalline berberine ascorbate Form B was analyzed by XRPD. The key peaks from the XRPD pattern are tabulated in Table 2 and the XRPD pattern is shown in FIG. 4.

TABLE 2

XRPD Peaks for Berberine Ascorbate Form B

| Angle (2θ ± 0.2°) | Intensity (%) |
|---|---|
| 6.9 | 100.0 |
| 14.8 | 82.7 |
| 15.8 | 60.6 |
| 25.2 | 37.4 |
| 26.4 | 22.4 |
| 25.7 | 20.0 |
| 20.7 | 18.1 |
| 19.1 | 15.5 |
| 27.7 | 15.0 |
| 20.2 | 14.8 |

Figure 5:
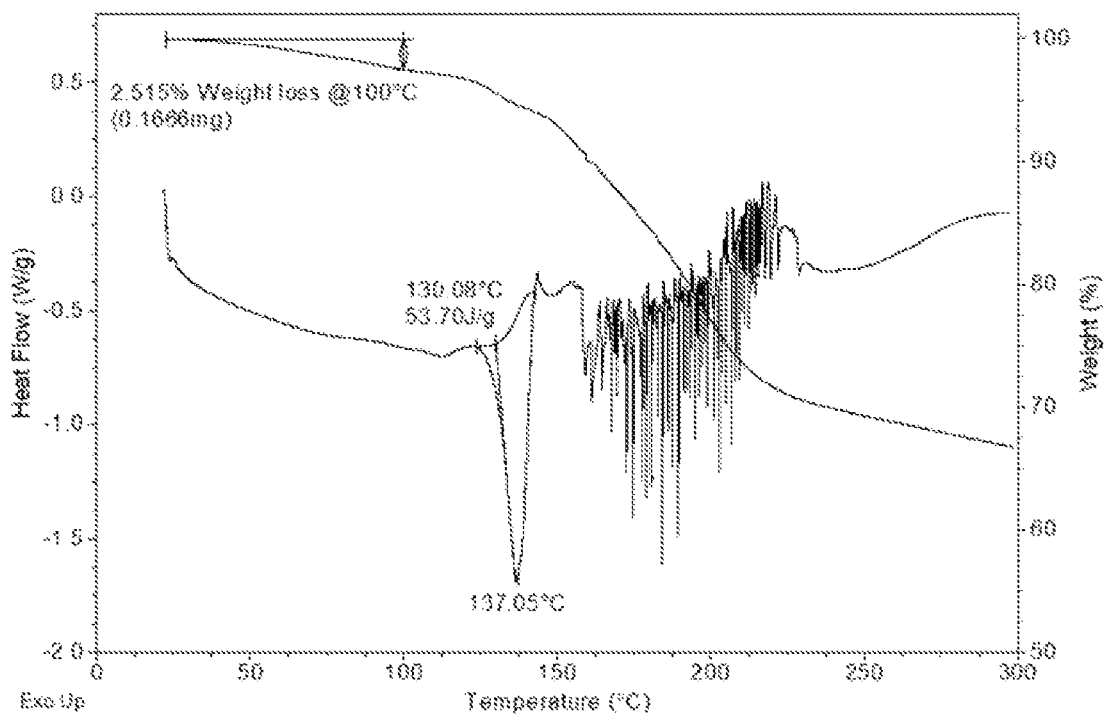
FIG. 5 shows the DSC/TGA diagrams of crystalline berberine ascorbate Form B.

Crystalline berberine ascorbate Form B was also analyzed by the thermal analysis techniques. DSC analysis indicates that Form B has an endotherm event of melting and decomposition with an onset at about 130° C. and a peak at about 137° C. TGA indicates that Form B exhibits a mass loss of 2.5% upon heating from about 25° C. to about 100° C. A representative DSC/TGA thermogram of crystalline berberine ascorbate Form B is shown in FIG. 5.

Example 3

Preparation and Characterization of an Exemplary Crystalline Berberine Ascorbate Form C About 20 mg of crystalline berberine ascorbate Form A (or Form B) was dissolved in about 1.0 ml of a mixture solvents of methanol/water (about 1:1, v/v). The yellow solution was evaporated at the room condition. Yellow crystalline solid was obtained after the solution was dried. Alternatively, ethanol/water, acetone/water, acetonitrile/water or tetrahydrofuran/water was used in evaporation recrystallization. Crystalline berberine ascorbate Form C was obtained.

Figure 6:
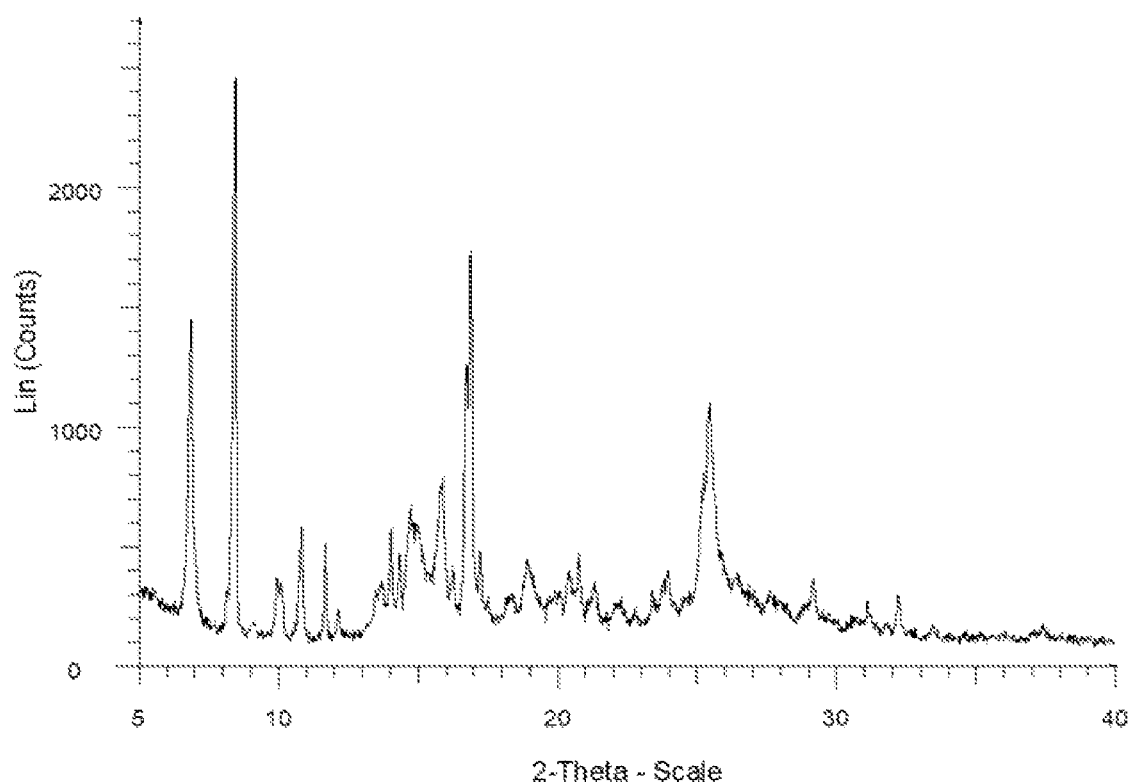
FIG. 6 shows the powder X-ray diffraction pattern of crystalline berberine ascorbate Form C.

Crystalline berberine ascorbate Form C was analyzed by XRPD. The key peaks from the XRPD pattern are tabulated in Table 3 and the XRPD pattern is shown in FIG. 6.

TABLE 3

XRPD Peaks for Berberine Ascorbate Form C

| Angle (2θ ± 0.2°) | Intensity (%) |
|---|---|
| 8.4 | 100.0 |
| 16.9 | 73.5 |
| 6.8 | 61.6 |
| 25.5 | 46.5 |
| 15.8 | 32.5 |
| 25.2 | 30.1 |
| 14.7 | 28.5 |
| 10.8 | 24.6 |
| 14.0 | 24.5 |
| 15.0 | 24.1 |

Single crystals of crystalline berberine ascorbate Form A were obtained by slow evaporation of the solutions of methanol/water, ethanol/water, or acetonitrile/water. Single crystal analysis of Form C confirms 1:1 counter ion ratio of berberine cation and a highly disordered ascorbate anion. Crystallographic data: monoclinic Pc space group, Z'=2, unit cell dimensions: a=8.4264(4) Å, b=10.5212(6) Å, c=26.523(1) Å, β=96.736(2) °, and V=2335.2(4) Å$^3$.

Example 4

Preparation and Characterization of an Exemplary Crystalline Berberine Ascorbate Form D About 50 mg of crystalline berberine ascorbate Form A was dissolved in about 1.0 ml of water. The yellow solution was evaporated in a container with desiccant at the room temperature. Yellow solid of crystalline berberine ascorbate Form D was obtained after the solution was dried.

Figure 7:
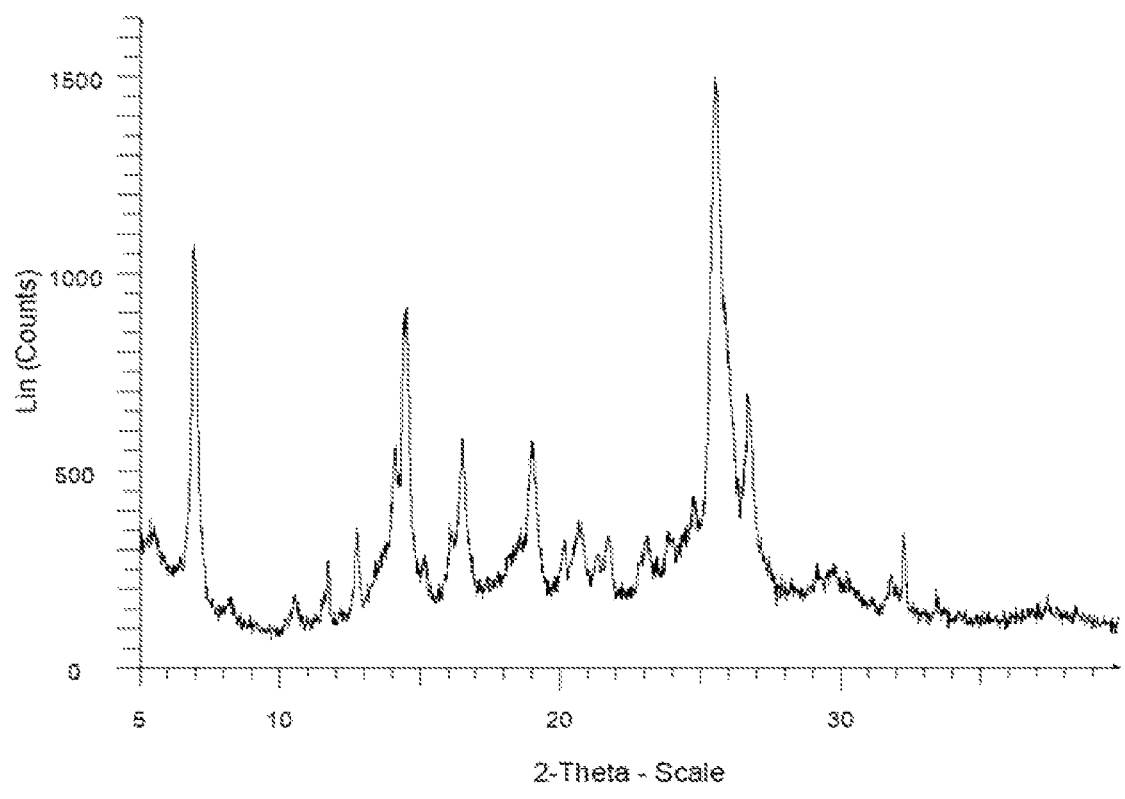
FIG. 7 shows the powder X-ray diffraction pattern of crystalline berberine ascorbate Form D.

Crystalline berberine ascorbate Form D was analyzed by XRPD. The key peaks from the XRPD pattern are tabulated in Table 4 and the XRPD pattern is shown in FIG. 7.

TABLE 4

XRPD Peaks for Berberine Ascorbate Form D

| Angle (2θ ± 0.2°) | Intensity (%) |
|---|---|
| 25.6 | 100.0 |
| 6.9 | 71.7 |
| 14.5 | 60.8 |
| 26.7 | 45.5 |
| 16.5 | 38.6 |
| 19.0 | 38.2 |
| 14.1 | 37.4 |
| 12.7 | 23.6 |
| 20.7 | 23.1 |
| 16.1 | 23.0 |

Example 5

Preparation and Characterization of an Exemplary Crystalline Berberine Acetone Adduct 407 mg of berberine chloride dihydrate (1.0 mmol) was suspended in 10.0 ml of methanol and stirred at the room temperature for about 30 minutes to obtain a homogenous slurry. To the suspension, 2.0 ml of 0.5 N NaOH aqueous solution was added, an orange-red solution was obtained. The solution was filtered, and 2.0 ml of acetone was added to obtain a clear solution. 4.0 ml of water was added slowly to the clear solution and the yellow solid started to precipitate. The suspension was stirred at the room temperature for about 1 hour to yield a homogenous slurry. The yellow solid was collected by filtration, washed with small amount of methanol/water (1:1, v/v), and then dried in the air. 295 mg of crystalline berberine acetone adduct was obtained. (75% yield).

Figure 8:
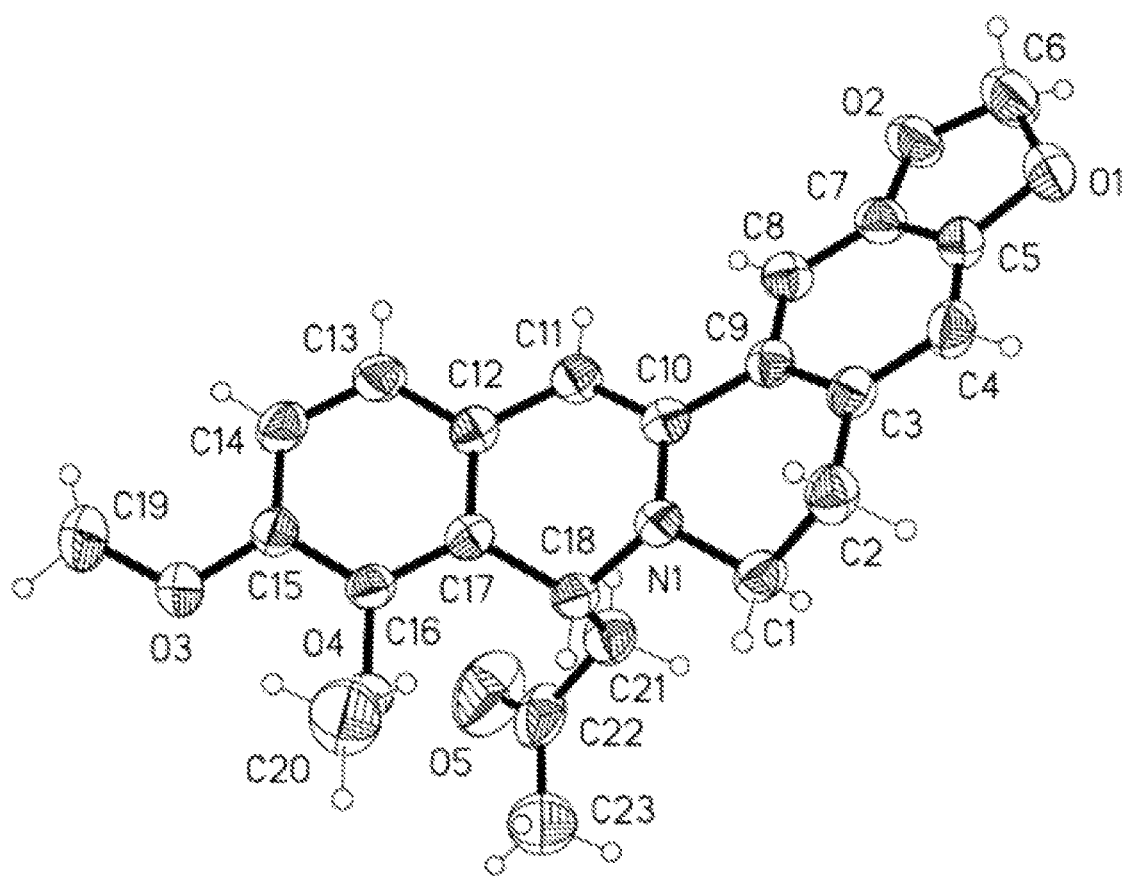
FIG. 8 shows the single crystal structure of crystalline berberine acetone adduct.

Single crystals of crystalline berberine acetone adduct were obtained by slow evaporation of the solution of acetone or acetonitrile. The single crystal structure is shown in FIG. 8. Crystallographic data: orthorhombic P2$_1$2$_1$2$_1$ space group, Z'=1, unit cell dimensions: a=6.292(2) Å, b=14.022(4) Å, c=22.584(7) Å, and V=1992.4(10) Å$^3$.

Figure 9:
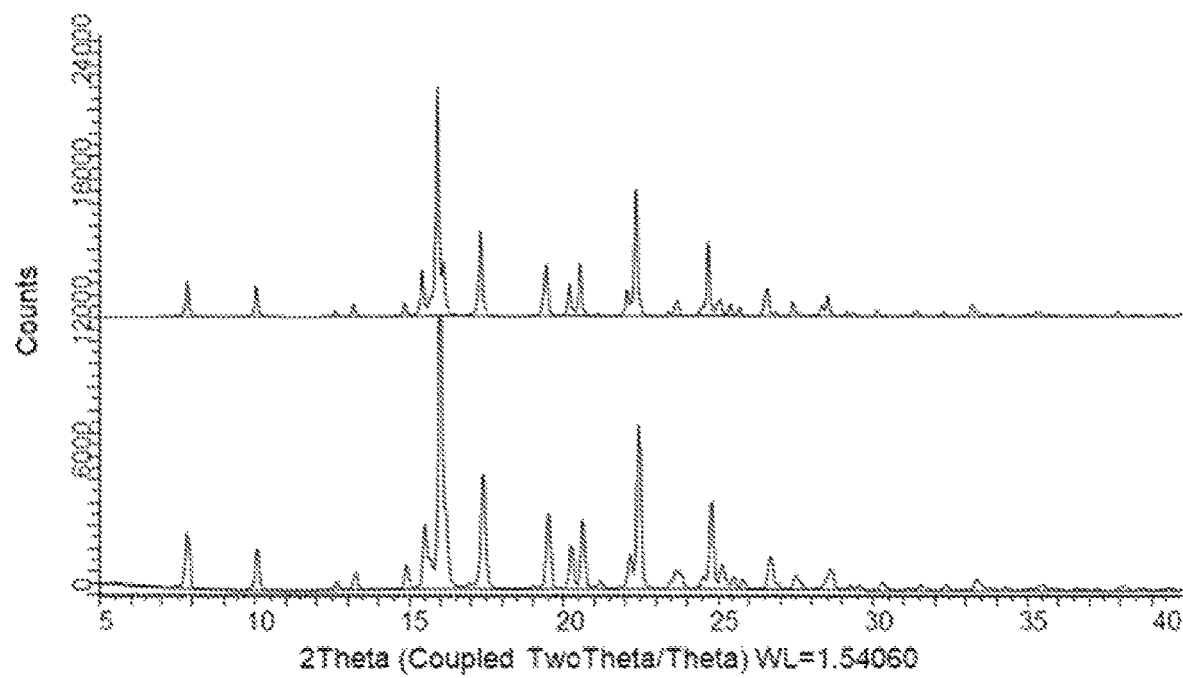
FIG. 9 shows the overlay of the simulated powder X-ray diffraction pattern (upper) and the experimental powder X-ray diffraction pattern (bottom) of crystalline berberine acetone adduct.
Figure 10:
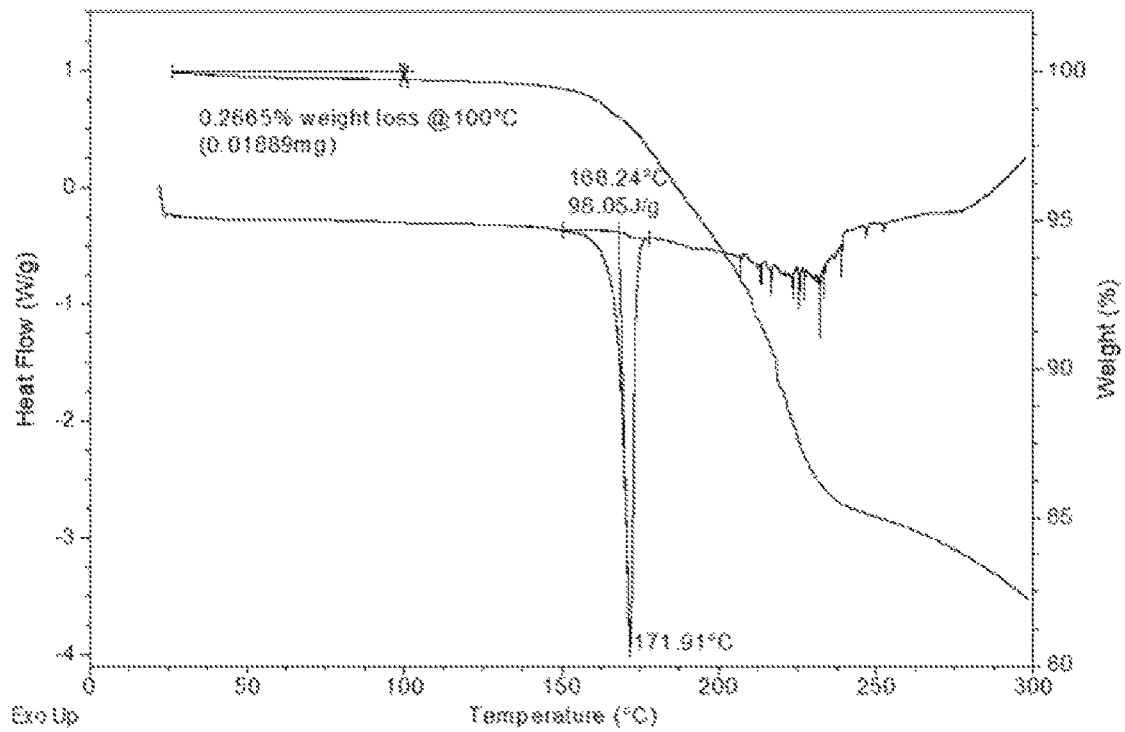
FIG. 10 shows the DSC/TGA diagrams of crystalline berberine acetone adduct.

A simulated powder X-ray diffraction pattern calculated from the single crystal structure of the crystalline berberine acetone adduct matches with the experimental powder X-ray diffraction pattern of the berberine acetone adduct bulk material, as shown in FIG. 9.

Crystalline berberine acetone adduct was also analyzed by the thermal analysis techniques. DSC analysis indicates that the adduct has an endotherm event of melting and decomposition with an onset at about 168° C. and a peak at about 172° C. TGA indicates that the adduct exhibits a mass loss of 0.3% upon heating from about 25° C. to about 100° C. A representative DSC/TGA thermogram of crystalline berberine ascorbate Form A is shown in FIG. 3.

Example 6

Preparation and Characterization of an Exemplary Crystalline Berberine Methyl Ethyl Ketone Adduct 410 mg of berberine chloride dihydrate (1.0 mmol) was suspended in 10.0 ml of methanol and stirred at the room temperature for about 30 minutes to obtain a homogenous slurry. To the suspension, 2.0 ml of 0.5 N NaOH aqueous solution was added, an orange-red solution was obtained. The solution was filtered, and 2.0 ml of methyl ethyl ketone (2-butanone) was added to obtain a clear solution. 4.0 ml of water was added slowly to the clear solution and the pale-yellow solid started to precipitate. The suspension was stirred at the room temperature for about 1 hour to yield a homogenous slurry. The pale-yellow solid was collected by filtration, washed with small amount of methanol/water (1:1, v/v), and then dried in the air. 284 mg of crystalline berberine methyl ethyl ketone adduct was obtained. (70% yield).

Figure 11:
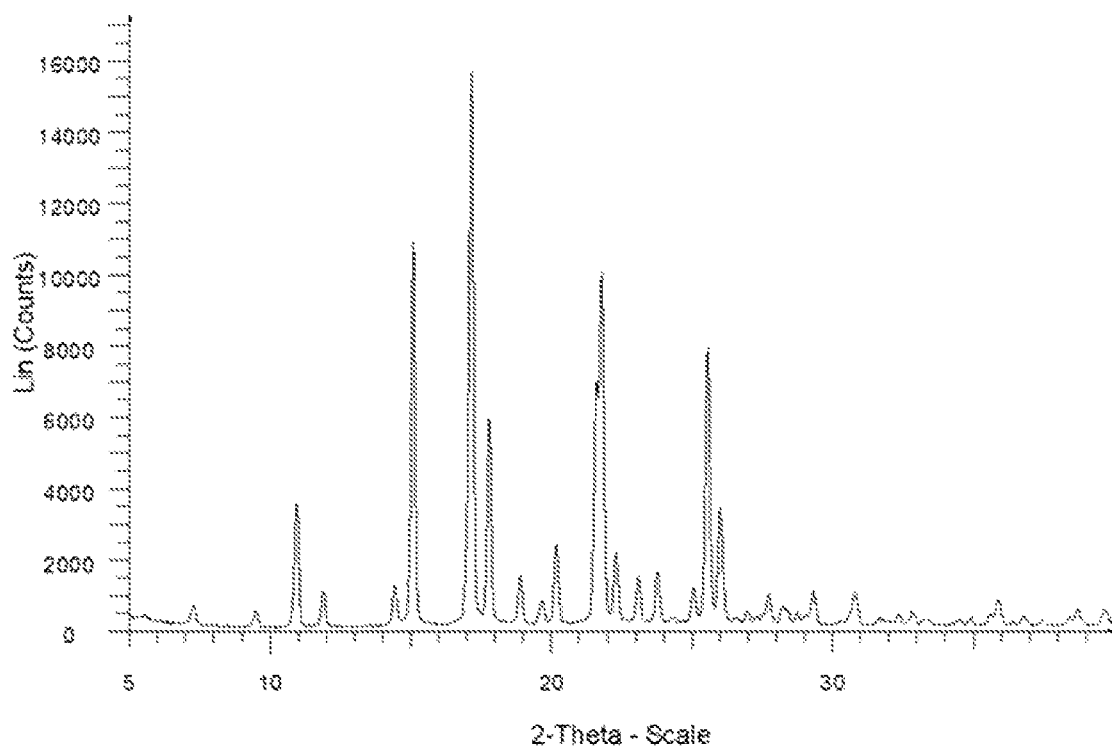
FIG. 11 shows the powder X-ray diffraction pattern of crystalline berberine methyl ethyl ketone adduct.

Crystalline berberine methyl ethyl ketone adduct was analyzed by XRPD. The key peaks from the XRPD pattern are tabulated in Table 5 and the XRPD pattern is shown in FIG. 11.

TABLE 5

XRPD Peaks for Crystalline Berberine Methyl Ethyl Ketone Adduct

| Angle (2θ ± 0.2°) | Intensity (%) |
|---|---|
| 17.1 | 100.0 |
| 15.1 | 69.6 |
| 21.8 | 64.0 |
| 25.6 | 50.6 |
| 21.6 | 44.8 |
| 17.8 | 37.9 |
| 10.9 | 22.8 |
| 26.0 | 22.1 |
| 20.2 | 15.3 |
| 22.3 | 13.9 |

Figure 12:
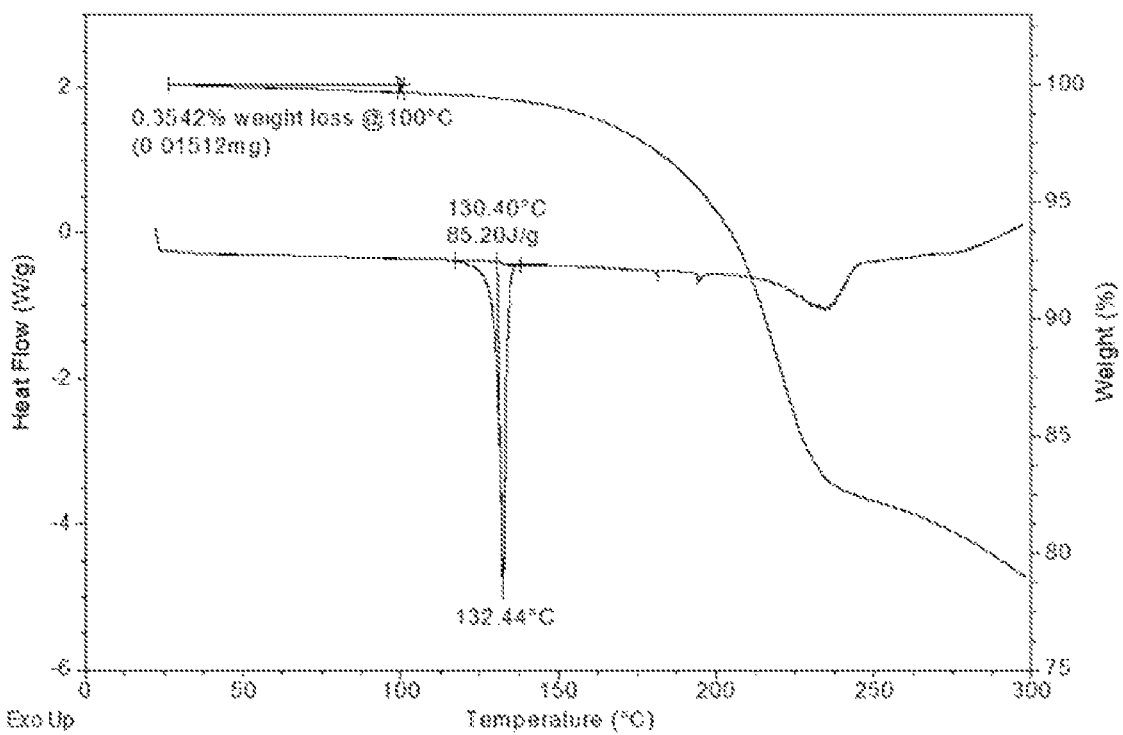
FIG. 12 shows the DSC/TGA diagrams of crystalline berberine methyl ethyl ketone adduct.

Crystalline berberine methyl ethyl ketone adduct was also analyzed by the thermal analysis techniques. DSC analysis indicates that the adduct has an endotherm event of a melting point with an onset at about 130° C. and a peak at about 132° C. TGA indicates that the adduct exhibits a mass loss of 0.4% upon heating from about 25° C. to about 100° C. A representative DSC/TGA thermogram of crystalline berberine methyl ethyl ketone adduct is shown in FIG. 12.

Example 7

Preparation and Characterization of an Exemplary Crystalline Berberine Methyl Phenyl Ketone Adduct 410 mg of berberine chloride dihydrate (1.0 mmol) was suspended in 10.0 ml of methanol and stirred at the room temperature for about 30 minutes to obtain a homogenous slurry. To the suspension, 2.0 ml of 0.5 N NaOH aqueous solution was added, an orange-red solution was obtained. The solution was filtered, and 2.0 ml of methyl phenyl ketone (acetophenone) was added to obtain a clear solution. 4.0 ml of water was added slowly to the clear solution and the yellow solid started to precipitate. The suspension was stirred at the room temperature for about 1 hour to yield a homogenous slurry. The yellow solid was collected by filtration, washed with small amount of methanol/water (1:1, v/v), and then dried in the air. 328 mg of crystalline berberine methyl phenyl ketone adduct was obtained. (72% yield).

Figure 13:
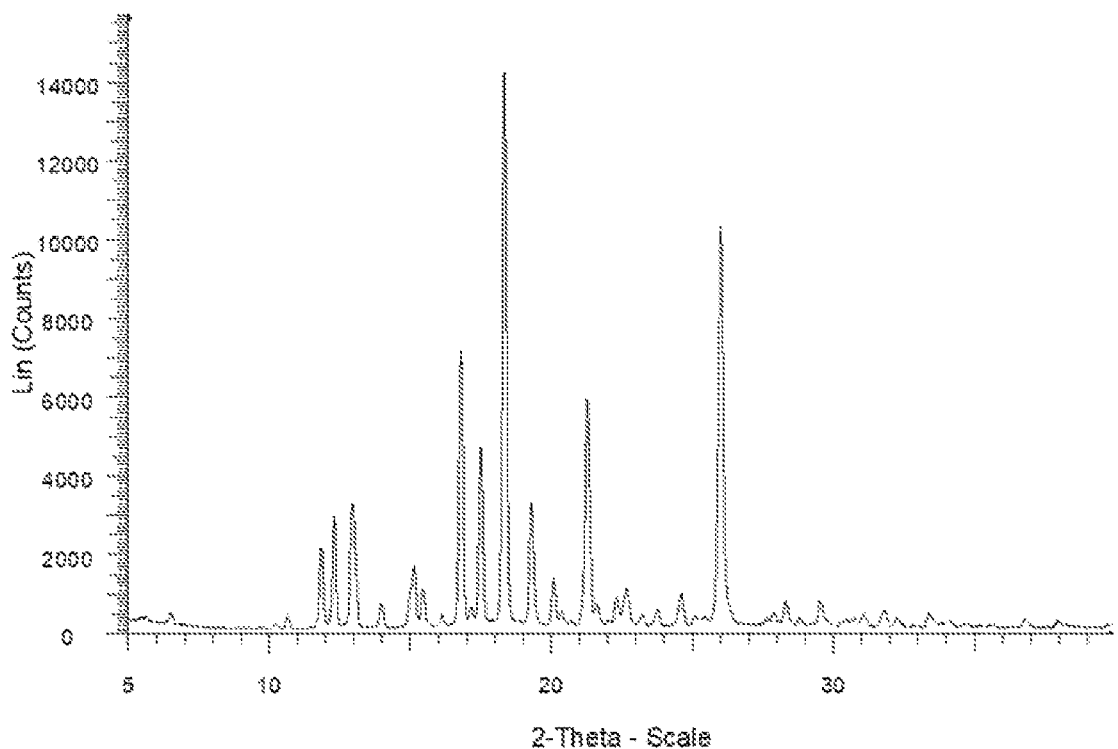
FIG. 13 shows the powder X-ray diffraction pattern of crystalline berberine methyl phenyl ketone adduct.

Crystalline berberine methyl phenyl ketone adduct was analyzed by XRPD. The key peaks from the XRPD pattern are tabulated in Table 6 and the XRPD pattern is shown in FIG. 13.

TABLE 6

XRPD Peaks for Crystalline Berberine Methyl Phenyl Ketone Adduct

| Angle (2θ ± 0.2°) | Intensity (%) |
|---|---|
| 18.3 | 100.0 |
| 26.0 | 72.2 |
| 16.8 | 50.2 |
| 21.3 | 41.7 |
| 17.5 | 32.9 |
| 19.3 | 23.3 |
| 12.9 | 22.9 |
| 12.3 | 20.7 |
| 11.8 | 15.2 |
| 15.1 | 12.2 |

Figure 14:
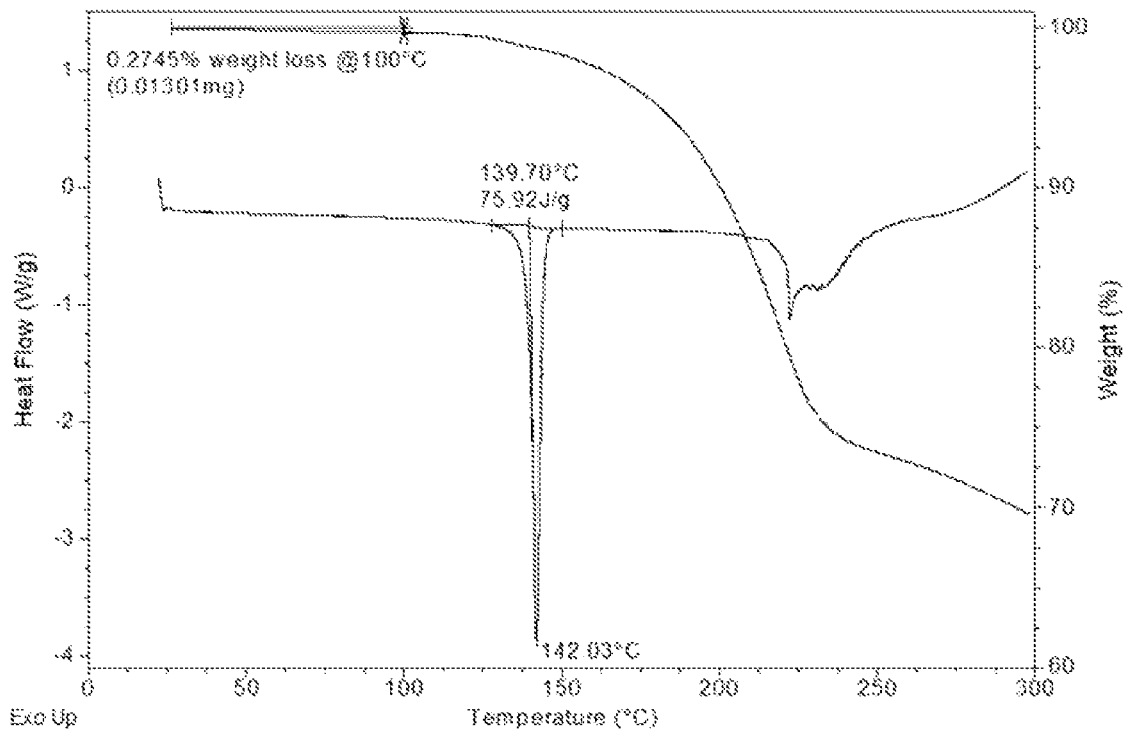
FIG. 14 shows the DSC/TGA diagrams of crystalline berberine methyl phenyl ketone adduct.

Crystalline berberine methyl phenyl ketone adduct was also analyzed by the thermal analysis techniques. DSC analysis indicates that the adduct has an endotherm event of a melting point with an onset at about 140° C. and a peak at about 142° C. TGA indicates that the adduct exhibits a mass loss of 0.3% upon heating from about 25° C. to about 100° C. A representative DSC/TGA thermogram of crystalline berberine methyl phenyl ketone adduct is shown in FIG. 14.

Example 8

Preparation and Characterization of an Exemplary Crystalline Berberine Methyl Isopropyl Ketone Adduct 410 mg of berberine chloride dihydrate (1.0 mmol) was suspended in 10.0 ml of methanol and stirred at the room temperature for about 30 minutes to obtain a homogenous slurry. To the suspension, 2.0 ml of 0.5 N NaOH aqueous solution was added, an orange-red solution was obtained. The solution was filtered, and 2.0 ml of methyl isopropyl ketone (3-methyl-2-butanone) was added to obtain a clear solution. 4.0 ml of water was added slowly to the clear solution and the pale-yellow solid started to precipitate. The suspension was stirred at the room temperature for about 1 hour to yield a homogenous slurry. The pale-yellow solid was collected by filtration, washed with small amount of methanol/water (1:1, v/v), and then dried in the air. 275 mg of crystalline berberine methyl ethyl ketone adduct was obtained. (65% yield).

Figure 15:
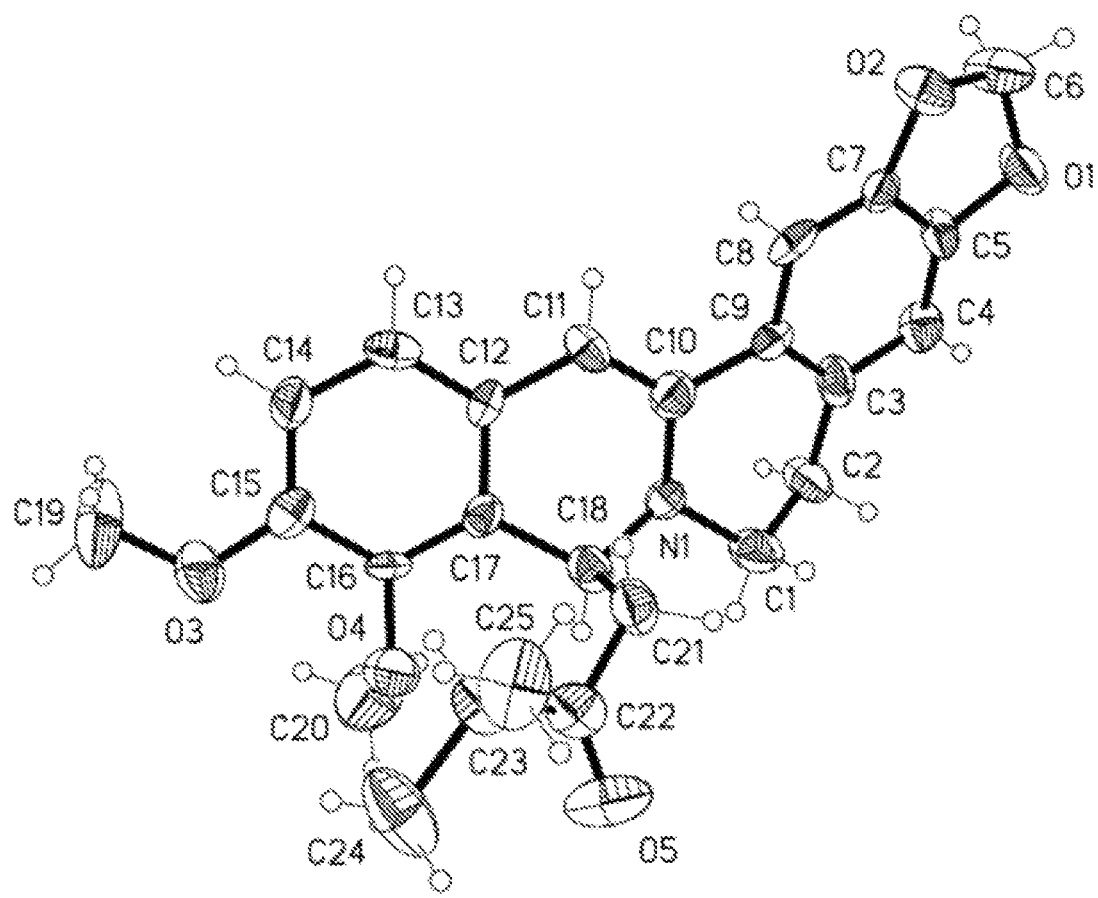
FIG. 15 shows the single crystal structure of crystalline berberine methyl isopropyl ketone adduct.

Single crystals of crystalline berberine methyl isopropyl ketone adduct were obtained by slow evaporation of the solution of acetonitrile. The single crystal structure is shown in FIG. 15. Crystallographic data: Monoclinic P2$_1$ space group, Z'=1, unit cell dimensions: a=10.4696(17) Å, b=6.5826(11) Å, c=15.733(3) Å, β=95.195(4) °, and V=1079.9(3) Å$^3$.

Figure 16:
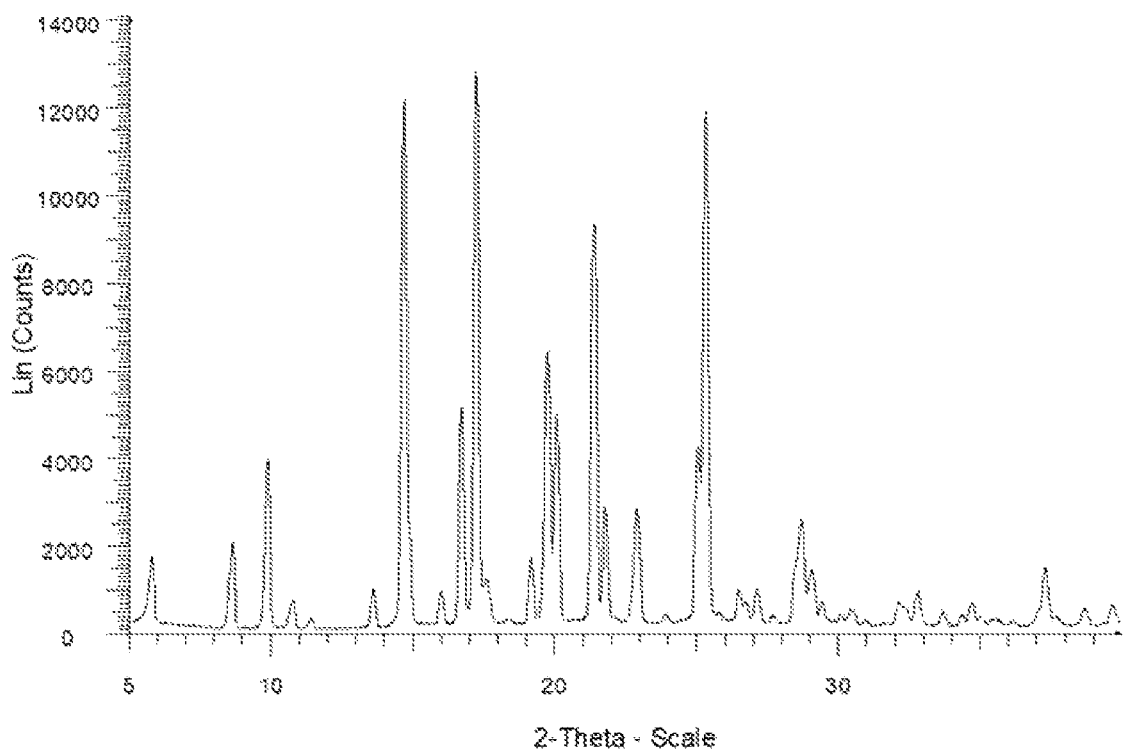
FIG. 16 shows the powder X-ray diffraction pattern of crystalline berberine methyl isopropyl ketone adduct.

Crystalline berberine methyl isopropyl ketone adduct was analyzed by XRPD. The key peaks from the XRPD pattern are tabulated in Table 7 and the XRPD pattern is shown in FIG. 16.

TABLE 7

XRPD Peaks for Crystalline Berberine
Methyl Isopropyl Ketone Adduct

| Angle (2θ ± 0.2°) | Intensity (%) |
|---|---|
| 17.2 | 100.0 |
| 14.7 | 95.2 |
| 25.3 | 93.6 |
| 21.4 | 73.0 |
| 19.8 | 50.4 |
| 16.7 | 40.2 |
| 20.1 | 39.1 |
| 9.9 | 30.9 |
| 25.0 | 30.2 |
| 21.8 | 22.6 |

A simulated powder X-ray diffraction pattern calculated from the single crystal structure of crystalline berberine methyl isopropyl ketone adduct matches with the experimental powder X-ray diffraction pattern of crystalline berberine methyl isopropyl ketone adduct bulk material.

Figure 17:
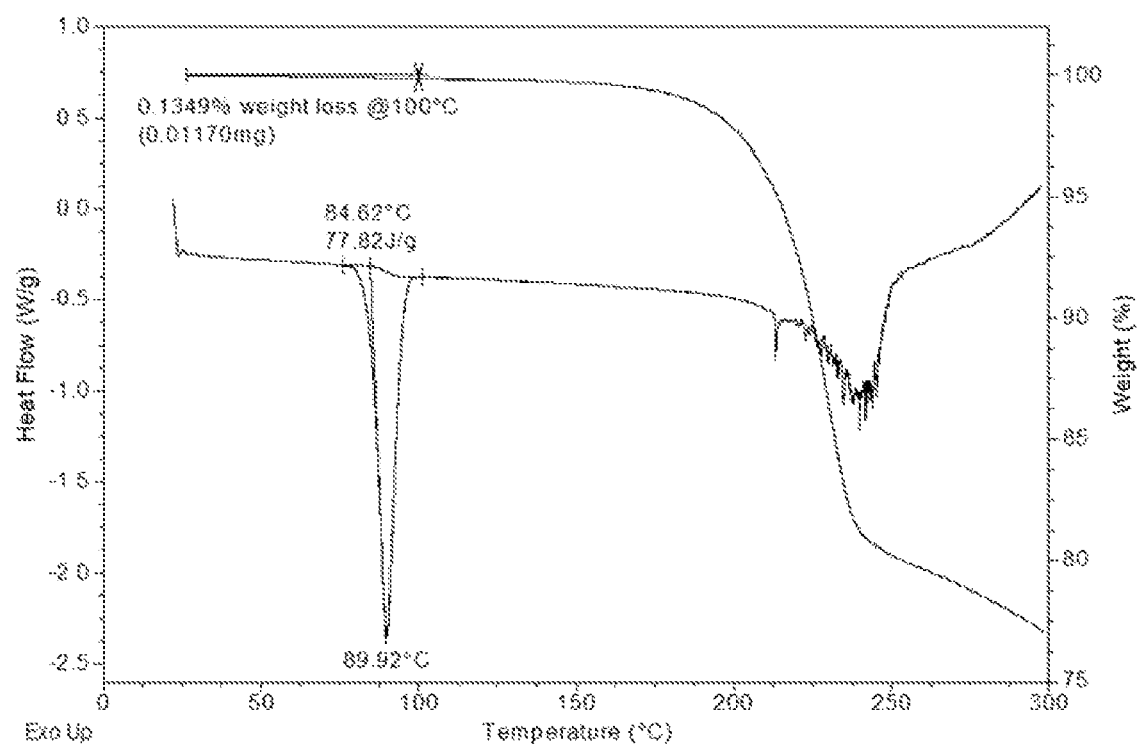
FIG. 17 shows the DSC/TGA diagrams of crystalline berberine methyl isopropyl ketone adduct.

Crystalline berberine methyl isopropyl ketone adduct was also analyzed by the thermal analysis techniques. DSC analysis indicates that the adduct has an endotherm event of a melting point with an onset at about 85° C. and a peak at about 90° C. TGA indicates that the adduct exhibits a mass loss of 0.1% upon heating from about 25° C. to about 100° C. A representative DSC/TGA thermogram of crystalline berberine methyl isopropyl ketone adduct is shown in FIG. 17.

Example 9

Preparation and Characterization of an Exemplary Crystalline Berberine Methyl Isobutyl Ketone Adduct 210 mg of berberine chloride dihydrate (0.50 mmol) was suspended in 5.0 ml of methanol and stirred at the room temperature for about 30 minutes to obtain a homogenous slurry. To the suspension, 1.0 ml of 0.5 N NaOH aqueous solution was added, an orange-red solution was obtained. The solution was filtered, and 1.0 ml of methyl isobutyl ketone (4-methyl-2-pentanone) was added to obtain a clear solution. 2.0 ml of water was added slowly to the clear solution and the pale-yellow solid started to precipitate. The suspension was stirred at the room temperature for about 1 hour to yield a homogenous slurry. The pale-yellow solid was collected by filtration, washed with small amount of methanol/water (1:1, v/v), and then dried in the air. 117 mg of crystalline berberine methyl ethyl ketone adduct was obtained. (51% yield).

Figure 18:
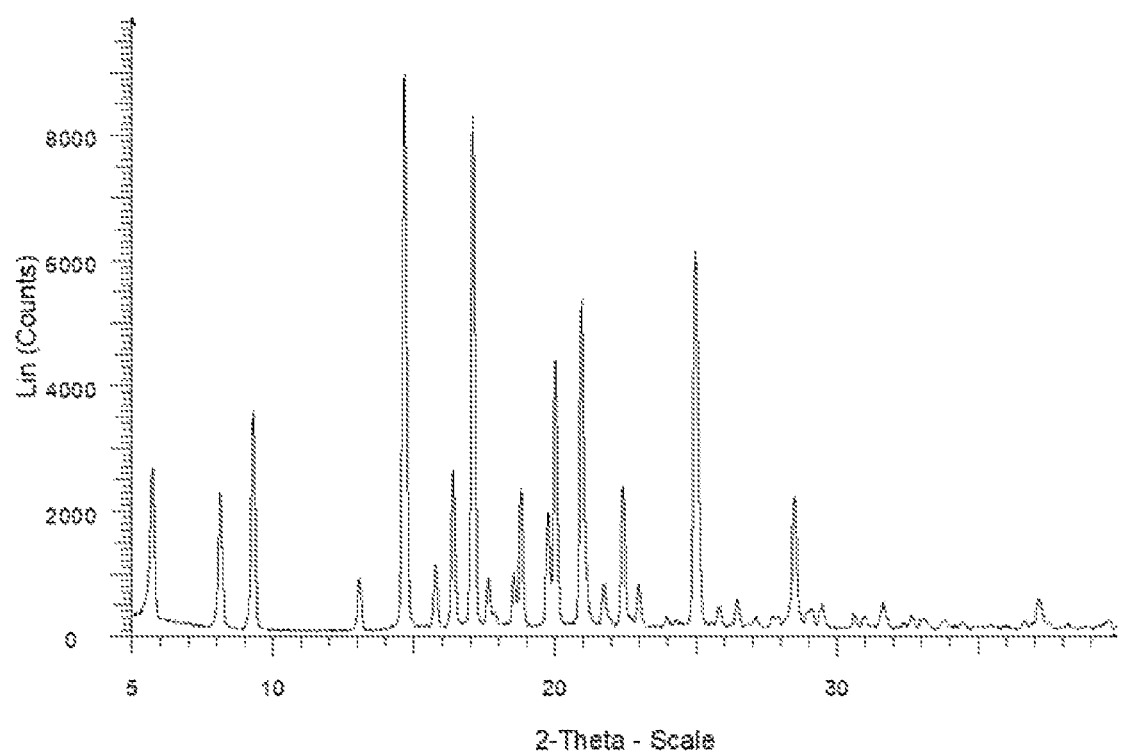
FIG. 18 shows the powder X-ray diffraction pattern of crystalline berberine methyl isobutyl ketone adduct.

Crystalline berberine methyl isobutyl ketone adduct was analyzed by XRPD. The key peaks from the XRPD pattern are tabulated in Table 8 and the XRPD pattern is shown in FIG. 18.

TABLE 8

XRPD Peaks for Crystalline Berberine
Methyl Isobuty Ketone Adduct

| Angle (2θ ± 0.2°) | Intensity (%) |
|---|---|
| 14.7 | 100.0 |
| 17.1 | 92.8 |
| 25.0 | 68.7 |
| 20.9 | 60.1 |
| 20.0 | 49.2 |
| 9.3 | 40.0 |
| 5.7 | 29.7 |
| 16.4 | 29.5 |
| 22.4 | 27.0 |
| 18.8 | 26.2 |

Figure 19:
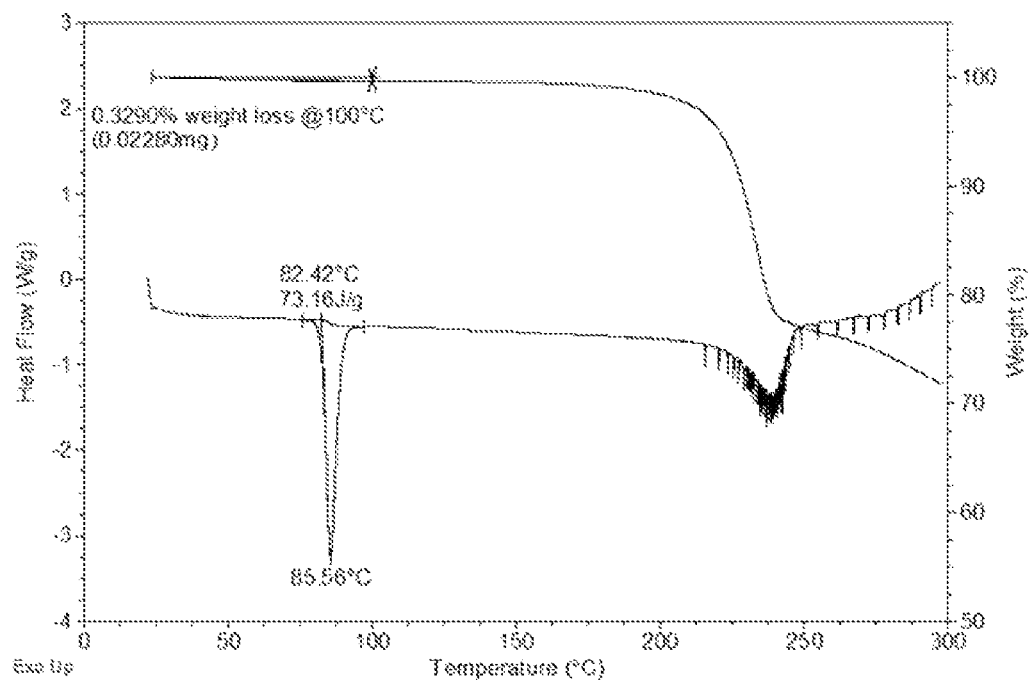
FIG. 19 shows the DSC/TGA diagrams of crystalline berberine methyl isobutyl ketone adduct.

Crystalline berberine methyl isobutyl ketone adduct was also analyzed by the thermal analysis techniques. DSC analysis indicates that the adduct has an endotherm event of a melting point with an onset at about 82° C. and a peak at about 86° C. TGA indicates that the adduct exhibits a mass loss of 0.3% upon heating from about 25° C. to about 100° C. A representative DSC/TGA thermogram of crystalline berberine methyl isobutyl ketone adduct is shown in FIG. 19.

Example 10

Preparation and Characterization of an Exemplary Crystalline Berberine Cyclohexanone Adduct 208 mg of berberine chloride dihydrate (0.50 mmol) was suspended in 5.0 ml of methanol and stirred at the room temperature for about 30 minutes to obtain a homogenous slurry. To the suspension, 1.0 ml of 0.5 N NaOH aqueous solution was added, an orange-red solution was obtained. After the solution was filtered, 1.0 ml of cyclohexanone was added slowly and the pale-yellow solid started to precipitate. 2.0 ml of water was added slowly, and the suspension was stirred at the room temperature for about 1 day to yield a homogenous slurry. The pale-yellow solid was collected by filtration, washed with small amount of methanol/water (1:1, v/v), and then dried in the air. 194 mg of crystalline berberine cyclohexanone adduct was obtained. (90% yield).

Figure 20:
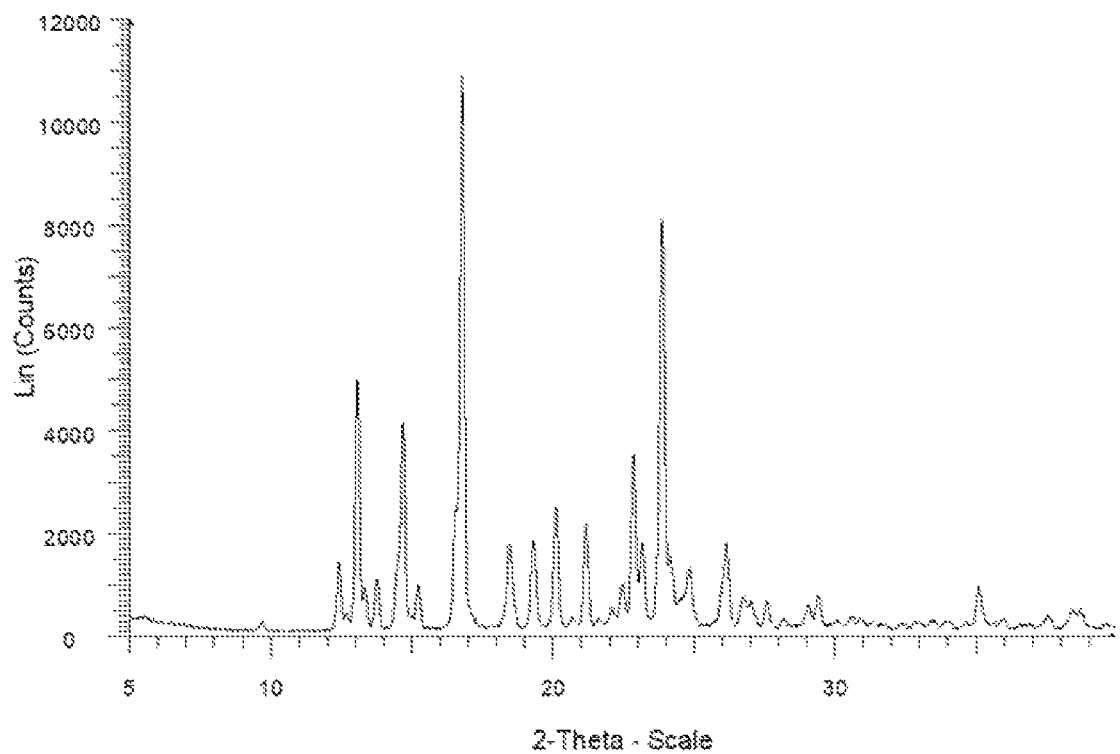
FIG. 20 shows the powder X-ray diffraction pattern of crystalline berberine cyclohexanone adduct.

Crystalline berberine cyclohexanone adduct was analyzed by XRPD. The key peaks from the XRPD pattern are tabulated in Table 9 and the XRPD pattern is shown in FIG. 20.

TABLE 9

XRPD Peaks for Crystalline
Berberine Cyclohexanone Adduct

| Angle (2θ ± 0.2°) | Intensity (%) |
|---|---|
| 16.8 | 100.0 |
| 23.9 | 74.6 |
| 13.0 | 45.6 |
| 14.7 | 38.1 |
| 22.9 | 32.3 |
| 20.1 | 23.2 |
| 16.5 | 22.5 |
| 21.2 | 19.7 |
| 19.3 | 17.2 |
| 26.2 | 16.6 |

Figure 21:
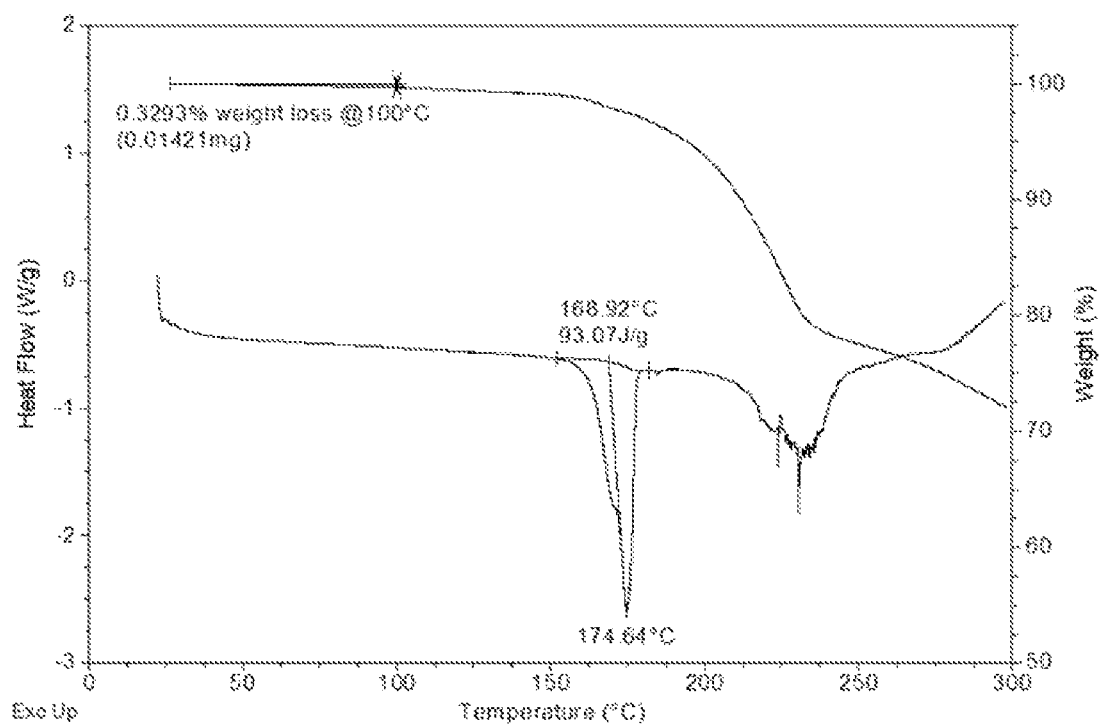
FIG. 21 shows the DSC/TGA diagrams of crystalline berberine cyclohexanone adduct.

Crystalline berberine cyclohexanone adduct was also analyzed by the thermal analysis techniques. DSC analysis indicates that the adduct has an endotherm event of a melting point with an onset at about 169° C. and a peak at about 175° C. TGA indicates that the adduct exhibits a mass loss of 0.3% upon heating from about 25° C. to about 100° C. A representative DSC/TGA thermogram of crystalline berberine cyclohexanone adduct is shown in FIG. 21.

Example 11

Figure 22:
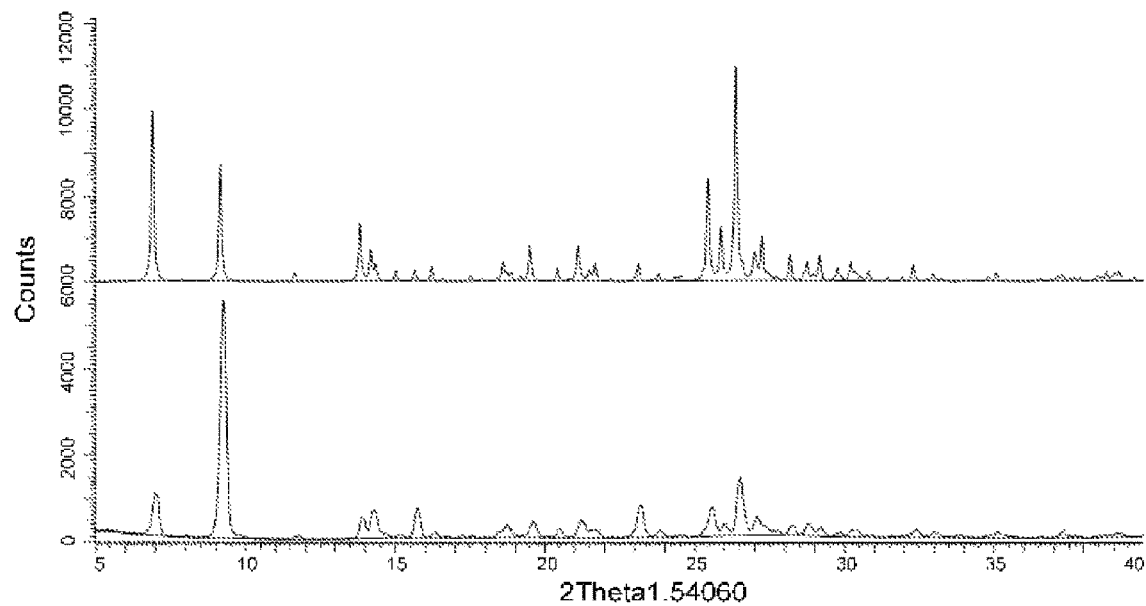
FIG. 22 shows the overlay of the simulated powder X-ray diffraction pattern (upper) and the experimental powder X-ray diffraction pattern (bottom) of berberine chloride tetrahydrate.

Reaction of Crystalline Berberine Ketone Adducts with Hydrochloric Acid
Method 1. Reaction of Berberine Acetone Adduct 39 mg of berberine acetone adduct (0.10 mmol) of one of berberine ketone adducts, was suspended in 1.1 ml of 0.10 N hydrochloric acid aqueous solution (0.11 mmol). The suspension was heated to about 80° C. and stirred for about 30 minutes, the yellow solid was converted to a yellow solid. A homogenous slurry was obtained after the suspension was cooled down to the room temperature and stirred for about 10 hours. The yellow solid was collected by filtration, washed with small amount of water, and then dried in the air. 21 mg of crystalline berberine chloride tetrahydrate was obtained. (48% yields). A simulated powder X-ray diffraction pattern calculated from the single crystal structure of crystalline berberine methyl isopropyl ketone adduct matches with the experimental powder X-ray diffraction pattern of crystalline berberine methyl isopropyl ketone adduct bulk material, as shown in FIG. 22.
Method 2. Reaction of Berberine Methyl Ethyl Ketone Adduct 41 mg of berberine methyl ethyl ketone adduct (0.10 mmol) was suspended in 1.1 ml of 0.10 N hydrochloric acid aqueous solution (0.11 mmol). The suspension was heated to about 80° C. and stirred for about 30 minutes, the yellow solid was converted to a yellow solid. A homogenous slurry was obtained after the suspension was cooled down to the room temperature and stirred for about 10 hours. The yellow solid was collected by filtration, washed with small amount of water, and then dried in the air. 21 mg of crystalline berberine chloride tetrahydrate was obtained. (48% yields).
Method 3. Reaction of Berberine Methyl Phenyl Ketone Adduct 46 mg of berberine methyl phenyl ketone adduct (0.10 mmol) was suspended in 1.1 ml of 0.10 N hydrochloric acid aqueous solution (0.11 mmol). The suspension was heated to about 80° C. and stirred for about 30 minutes, a clear yellow solution was obtained. A homogenous slurry was obtained after the suspension was cooled down to the room temperature and stirred for about 10 hours. The yellow solid was collected by filtration, washed with small amount of water, and then dried in the air. 30 mg of crystalline berberine chloride tetrahydrate was obtained. (68% yields).
Method 4. Reaction of Berberine Methyl Isopropyl Ketone Adduct 44 mg of berberine methyl isopropyl ketone adduct (0.10 mmol) was suspended in 1.1 ml of 0.10 N hydrochloric acid aqueous solution (0.11 mmol). The suspension was heated to about 80° C. and stirred for about 30 minutes, a clear yellow solution was obtained in about 15 minutes and then yellow solid started to precipitate. A homogenous slurry was obtained after the suspension was cooled down to the room temperature and stirred for about 10 hours. The yellow solid was collected by filtration, washed with small amount of water, and then dried in the air. 35 mg of crystalline berberine chloride tetrahydrate was obtained. (79% yields).
Method 5. Reaction of Berberine Methyl Isobutyl Ketone Adduct 46 mg of berberine methyl isobutyl ketone adduct (0.10 mmol) was suspended in 1.1 ml of 0.10 N hydrochloric acid aqueous solution (0.11 mmol). The suspension was heated to about 80° C. and stirred for about 30 minutes, a clear yellow solution was obtained in about 15 minutes and then yellow solid started to precipitate. A homogenous slurry was obtained after the suspension was cooled down to the room temperature and stirred for about 10 hours. The yellow solid was collected by filtration, washed with small amount of water, and then dried in the air. 38 mg of crystalline berberine chloride tetrahydrate was obtained. (86% yields).
Method 6. Reaction of Berberine Cyclohexanone Adduct 43 mg of berberine methyl cyclohexanone adduct (0.10 mmol) was suspended in 1.1 ml of 0.10 N hydrochloric acid aqueous solution (0.11 mmol). The suspension was heated to about 80° C. and stirred for about 30 minutes, the pale-yellow solid converted to a yellow solid. A homogenous slurry was obtained after the suspension was cooled down to the room temperature and stirred for about 10 hours. The yellow solid was collected by filtration, washed with small amount of water, and then dried in the air. 18 mg of crystalline berberine chloride tetrahydrate was obtained. (41% yields).

Example 12

Solubility Measurement of Berberine Ascorbate and Berberine Chloride 50 mg of crystalline berberine ascorbate Form A (from example 1) was suspended in 0.20 ml of water. A clear yellow solution was obtained within 15 minutes. The solution retained after stirring at the room temperature for 1 about day. The solubility of crystalline ascorbate Form A in water at the room temperature (about 22° C.) is more than 250 g/L.

Figure 23:
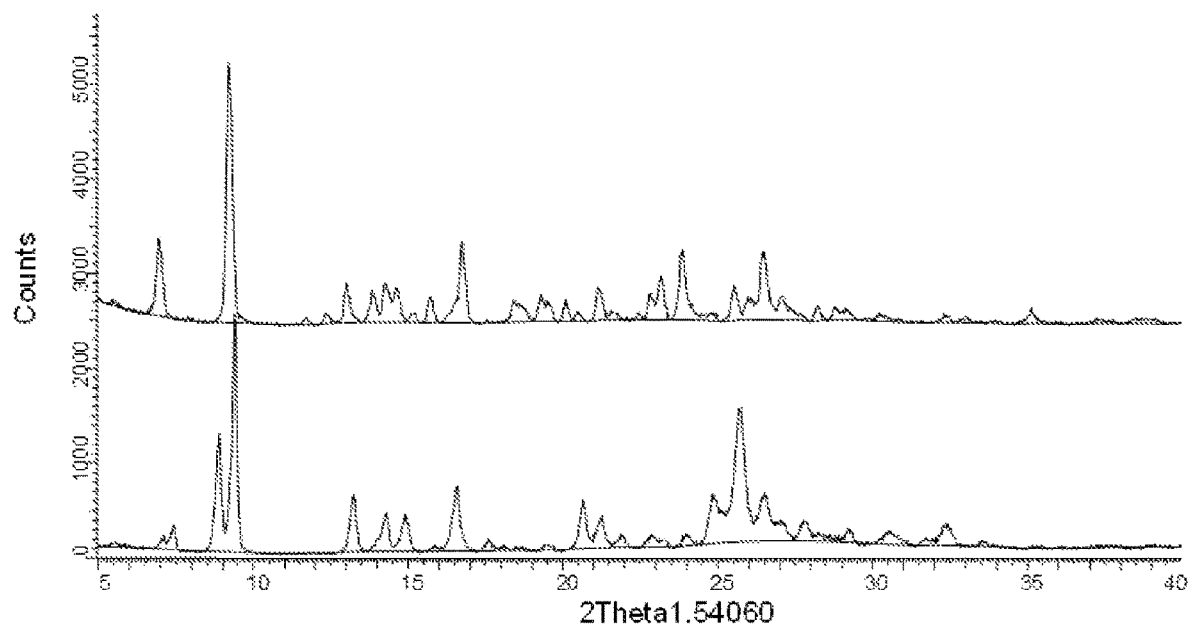
FIG. 23 shows the powder X-ray diffraction pattern overlay of solubility residue of berberine chloride tetrahydrate (upper) and starting material of berberine chloride dihydrate (bottom).

50 mg of crystalline berberine chloride dihydrate (from Sigma-Aldrich) was suspended in 10 ml of water. The yellow solid partially dissolved, and a homogenous yellow suspension was obtained after stirring at the room temperature for 1 about day. The solubility of berberine chloride in water at the room temperature (about 22° C.) is less than 5 g/L (Literature value: "The aqueous solubility of berberine chloride at 25° C. was determined to be 1.96±0.11 mg/mL" from AAPS PharmSciTech, 2010, 11(3), 1466-1475). The solubility residue was isolated by filtration. Powder X-ray pattern demonstrated that berberine chloride dihydrate converted berberine chloride tetrahydrate, as shown in FIG. 23.

Example 13

Preparation and Characterization of Amorphous Berberine Ascorbate

This preparation of berberine ascorbate was carried out according to the literature method in reference: Doklady Akademii Nauk Tadzhikskoi SSR, 1963, 6(6), 36-38.

Figure 24:
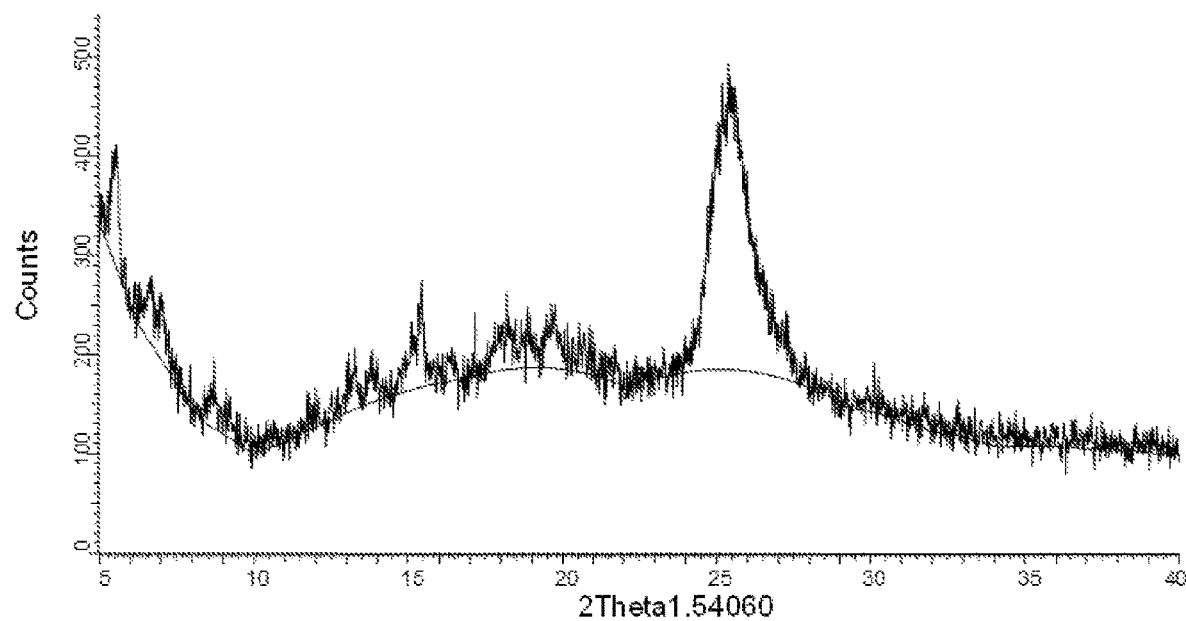
FIG. 24 shows the powder X-ray diffraction pattern of amorphous berberine ascorbate salt.

40 mg of berberine chloride (0.10 mmol) was suspended in 10.0 ml of water, 1.0 ml of 0.5 N sodium hydroxide aqueous solution was added with stirring, and a brown solution was obtained. The brown aqueous solution was extracted with 10 ml of ether for 3 times (total: 30 ml of ether). The ether solution was filtered. A solution of 16 mg of ascorbic acid (0.10 mmol) in 5 ml of methanol was added into the yellow ether solution. The resulting solution was evaporated to dry to obtain a brown gel-like solid. The resulting solid was stirred in 1.0 ml of ethanol at the room temperature for 1 day, 18 mg of brownish-yellow solid was obtained. Powder X-ray diffraction pattern confirmed that the solid was an amorphous material, as shown in FIG. 24. No crystalline berberine ascorbate was obtained by several attempts, and a high level of chemical impurities was also identified by NMR. Attempts to recrystallize berberine ascorbate only produced amorphous gel-like solids or glass-like solids.

Example 14

Reaction of Berberine Chloride with Sodium Ascorbic Acid in Water

This preparation method was similar to one for the preparation of berberine saccharine salt in reference: Cryst. Growth Des. 2016, 16, 933-939. (Berberine chloride, instead of the desired berberine ascorbate, precipitated out from the reaction mixture.)

41 mg of berberine chloride (0.10 mmol) was suspended in 5 ml of water. The suspension was heated to 80° C. for about 1 hour to get a clear yellow solution. 20 mg of sodium ascorbate (0.10 mmol) was added to the solution and the solid sodium ascorbate was dissolved in the solution. The resulting solution was stirred at 80° C. and then cooled down to the room temperature. Yellow solid started to precipitate, and the suspension was stirred at the room temperature for 1 day to obtain a homogenous yellow slurry. 16 mg of yellow solid was obtained after filtration and air-dried. Powder X-ray diffraction pattern confirmed that the yellow solid was berberine chloride tetrahydrate, instead of crystalline berberine ascorbate. This method did not produce the desired berberine ascorbate salt is since starting material of berberine chloride has much lower aqueous solubility compared to that of berberine ascorbate.

What is claimed is:

1. A crystalline form of a berberine ascorbate salt, wherein the salt has berberine as a cation and L-ascorbate as an anion, wherein the salt has a molar ratio of the berberine and the L-ascorbate from 0.9:1 to 1:0.9; wherein the salt is a solid of at least 75% crystalline material; wherein the berberine has the structure of:

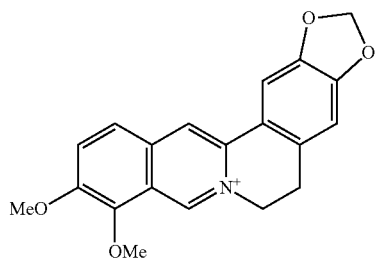 [SMILES: COc1ccc2cc3[n+](cc2c1OC)CCc1cc2c(cc1-3)OCO2]

and the L-ascorbate has the structure of:

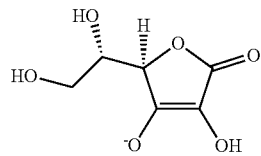

wherein the crystalline form is Form A, Form B, Form C or Form D; wherein Form A is characterized by an XRPD pattern comprising one or more peaks expressed as 2θ±0.2° of about 6.7°, about 8.6°, about 13.3°, about 15.5°, about 16.4°, about 17.8°, about 18.9°, about 19.7°, about 25.1°, and about 26.2°; wherein Form B is characterized by an XRPD pattern comprising one or more peaks expressed as 2θ±0.2° of about 6.9°, about 14.8°, about 15.8°, about 19.1°, about 20.2°, about 20.7°, about 25.2°, about 25.7°, about 26.4°, and about 27.7°; wherein Form C is characterized by an XRPD pattern comprising one or more peaks expressed as 2θ±0.2° of about 6.8°, about 8.4°, about 10.8°, about 14.0°, about 14.7°, about 15.0°, about 15.8°, about 16.9°, about 25.2°, and about 25.5°; and wherein Form D is characterized by an XRPD pattern comprising one or more peaks expressed as 2θ±0.2° of about 6.9°, about 12.7°, about 14.1°, about 14.5°, about 16.1°, about 16.5°, about 19.0°, about 20.7°, about 25.6°, and about 26.7°.

2. The crystalline form according to claim 1, wherein the crystalline form is Form A.

3. The crystalline form according to claim 1, wherein the crystalline form is Form B.

4. The crystalline form according to claim 1, wherein the crystalline form is Form C.

5. The crystalline form according to claim 1, wherein the crystalline form is Form D.

6. A composition comprising the crystalline form according to claim 1, and a pharmaceutically acceptable carrier.

7. The composition according to claim 6, wherein the carrier is a diluent, adjuvant, excipient, vehicle, or mixture thereof.

8. The composition according to claim 6, wherein the composition is formulated into tablets, gel caps, capsules, pills, powders, granulates, suspensions, emulsions, solutions, gels, hydrogels, oral gels, pastes, eye drops, ointments, creams, plasters, drenches, delivery devices, suppositories, enemas, injectables, implants, sprays, or aerosols.

9. A method of therapeutic treatment of bacterial infection, or cardiovascular diseases or conditions comprising administering a therapeutically effective amount of the crystalline form according to claim 1 to a subject in need of.

10. A method of preparing the crystalline form according to claim 1, wherein the crystalline form is Form A or Form B and the method comprising: mixing a crystalline berberine ketone adduct of Formula (I) and an L-ascorbic acid

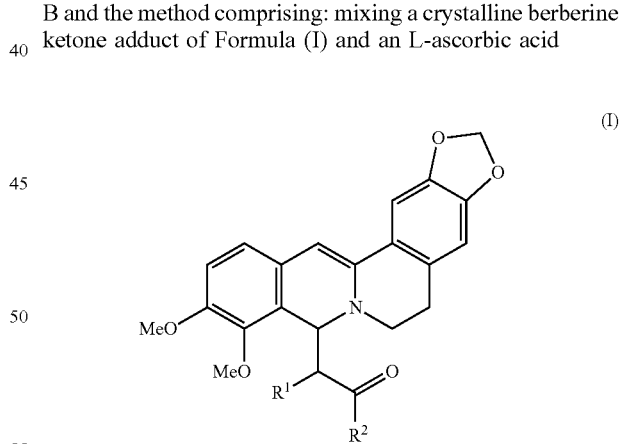

wherein $R^1$ is H, or a $C_1$-$C_5$ alkyl group and $R^2$ is a substituted or unsubstituted $C_1$-$C_{10}$ alkyl group or a substituted or unsubstituted aryl group; or $R^1$ and $R^2$ together form a substituted or unsubstituted methylene group, or a substituted or unsubstituted $C_2$-$C_6$ alkylene group.

11. The method according to claim 10, wherein $R^1$ is H and $R^2$ is methyl, ethyl, phenyl, isopropyl, or isobutyl, or $R^1$ and $R^2$ together form —$(CH_2)_4$—.

* * * * *